United States Patent
Shim et al.

(10) Patent No.: US 9,462,633 B2
(45) Date of Patent: Oct. 4, 2016

(54) MOBILE TERMINAL OPERATION CONTROLLED BY PROXIMITY SENSORS AND HEART RATE MONITOR

(71) Applicant: LG ELECTRONICS INC., Seoul (KR)

(72) Inventors: Hongjo Shim, Seoul (KR); Dongsu Han, Seoul (KR); Juno Yoon, Seoul (KR); Seonghyok Kim, Seoul (KR); Hyunwoo Kim, Seoul (KR); Gukchan Lim, Seoul (KR); Youngho Sohn, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 139 days.

(21) Appl. No.: 14/455,380

(22) Filed: Aug. 8, 2014

(65) Prior Publication Data

US 2015/0201065 A1    Jul. 16, 2015

(30) Foreign Application Priority Data

Jan. 14, 2014  (KR) .................. 10-2014-0004782

(51) Int. Cl.
*H04W 88/02* (2009.01)
*H04M 1/725* (2006.01)
*A61B 5/024* (2006.01)

(52) U.S. Cl.
CPC .............. *H04W 88/02* (2013.01); *A61B 5/024* (2013.01); *H04M 1/72569* (2013.01)

(58) Field of Classification Search
None
See application file for complete search history.

(56) References Cited

U.S. PATENT DOCUMENTS

| 2009/0209293 | A1* | 8/2009 | Louch | H04M 1/6041 455/566 |
| 2011/0312349 | A1* | 12/2011 | Forutanpour | G06F 1/1626 455/466 |
| 2014/0127996 | A1* | 5/2014 | Park | H04W 4/027 455/41.1 |
| 2014/0206327 | A1* | 7/2014 | Ziemianska | H04W 8/22 455/418 |
| 2015/0296065 | A1* | 10/2015 | Narita | H04W 88/02 455/556.2 |

\* cited by examiner

*Primary Examiner* — Philip Sobutka
(74) *Attorney, Agent, or Firm* — Birch, Stewart, Kolasch & Birch, LLP

(57) ABSTRACT

Provided is a mobile terminal. The mobile terminal includes: a display unit disposed at a front of the mobile terminal; a front proximity sensor disposed at the front of the mobile terminal; a back proximity sensor disposed at a back of the mobile terminal; and a control unit performing an operation by using a detection result of the back proximity sensor.

18 Claims, 48 Drawing Sheets

29a

FIG. 34
| Peaceful | Stress |
|----------|--------|
| Music    | Phone  |
| Movie    | Email  |
| Internet | Movie  |
34a
34b
FIG. 35A
| Phone | Call with John<br>(2013/01/01,14:00'~' 14:05) | Auto Recorded   Strongly Stressed |
|-------|----------------------------------------------|-----------------------------------|
|       | Call with James<br>(2013/01/01,15:00'~' 15:05) | Auto Recorded   Stressed         |
FIG. 35B
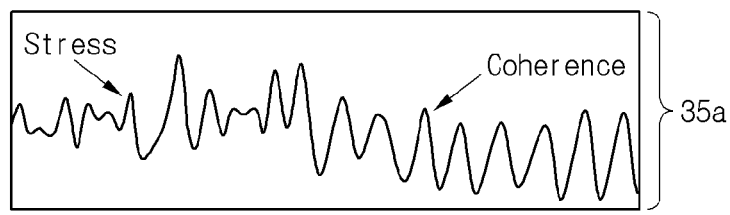
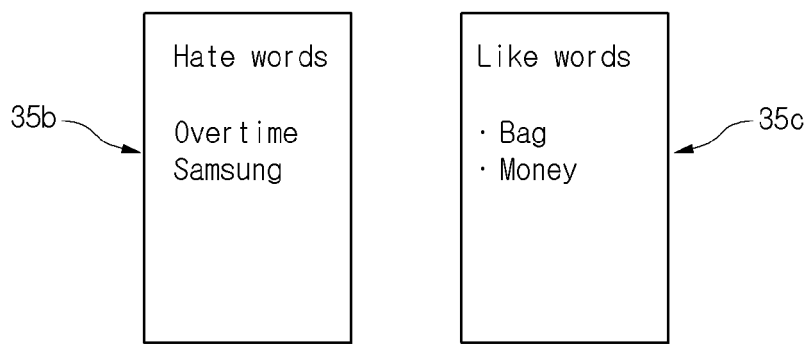
35b — Hate words: Overtime, Samsung
35c — Like words: Bag, Money

| Music | Say You Will<br>(2013/01/02, 13:00'~' 13:01) | Auto Checked | Very Peaceful |
| --- | --- | --- | --- |
| | Say You Will<br>(2013/01/02, 13:03'~' 13:04) | Auto Checked | Peaceful |

MOBILE TERMINAL OPERATION CONTROLLED BY PROXIMITY SENSORS AND HEART RATE MONITOR

CROSS-REFERENCE TO RELATED APPLICATIONS

This application claims the benefit under 35 U.S.C. §119 of Korean Patent Application No. 10-2014-0004782, filed Jan. 14, 2014, which is hereby incorporated by reference in its entirety.

BACKGROUND

The present disclosure relates to a mobile terminal.

Depending on whether terminals are movable, the terminals are divided into mobile/portable terminals and stationary terminals. Again, the mobile terminals may be divided into handheld terminals and vehicle mounted terminals depending on whether users can carry the mobile terminals personally.

Functions of the mobile terminals become diversified. For example, the functions include data and voice communication, picture capturing and video recording through a camera, voice recording, music file playback through a speaker system, and image or video output to a display unit. Some terminals may have an additional electronic game play function or a multimedia player function. Especially, recent mobile terminals may receive multicast signals providing visual contents such as broadcasts and video or television programs.

As functions of a terminal are diversified, such a terminal may be implemented in a form of a multimedia player having multi-functions, for example, photo or video capturing, playback of music or video files, game plays, and broadcast reception.

In order to support and increase functions of such a terminal, it is considered to improve structural part and/or software part of a terminal.

SUMMARY

Embodiments provide a terminal providing various functions by performing an operation in accordance with a given situation and an operating method thereof.

In one embodiment, a mobile terminal includes: a display unit disposed at a front of the mobile terminal; a front proximity sensor disposed at the front of the mobile terminal; a back proximity sensor disposed at a back of the mobile terminal; and a control unit performing an operation by using a detection result of the back proximity sensor.

In another embodiment, a mobile terminal includes: a display unit disposed at a front of the mobile terminal; a proximity sensor disposed at the front of the mobile terminal; a heart rate sensor disposed at a back of the mobile terminal and measuring a PPG signal by emitting light to a body portion of a user; and a control unit checking a user's heart rate from the PPG signal measured by the heart rate sensor and according thereto, controlling an operation of the mobile terminal.

The details of one or more embodiments are set forth in the accompanying drawings and the description below. Other features will be apparent from the description and drawings, and from the claims.

BRIEF DESCRIPTION OF THE DRAWINGS

FIG. 34 is a view illustrating statistics on heart rate information measured by a mobile terminal according to an embodiment of the present invention.

DETAILED DESCRIPTION OF THE EMBODIMENTS

Figure 1A:
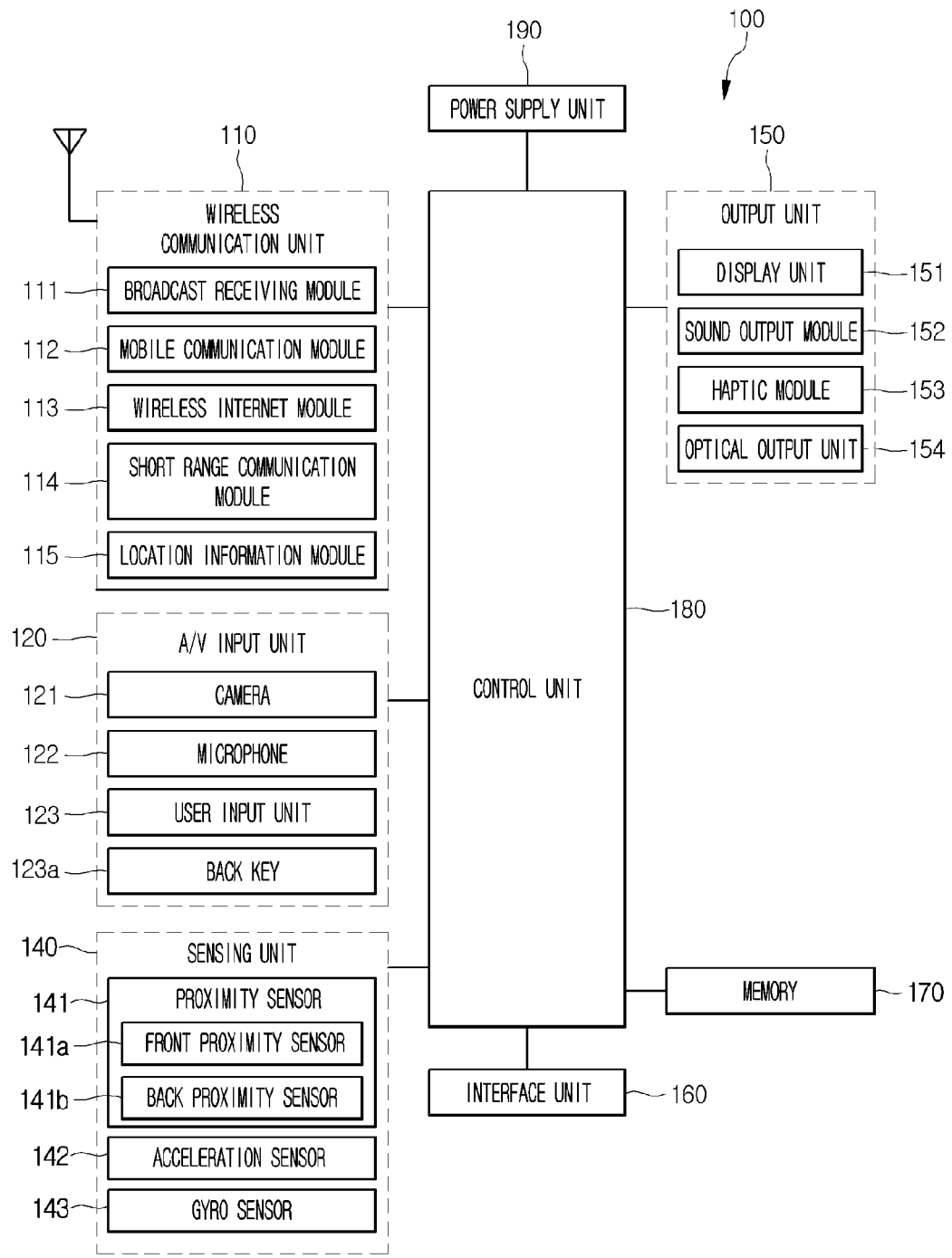
FIG. 1A is a block diagram illustrating a mobile terminal according to an embodiment of the present invention.

Hereinafter, embodiments of the present invention are described in more detail with reference to accompanying drawings and regardless of the drawings symbols, same or similar components are assigned with the same reference numerals and thus overlapping descriptions for those are omitted. The suffixes "module" and "unit" for components used in the description below are assigned or mixed in consideration of easiness in writing the specification and, do not have distinctive meanings or roles by themselves. In the following description, detailed descriptions of well-known functions or constructions will be omitted since they would obscure the invention in unnecessary detail. Additionally, the accompanying drawings are used to help easily understanding embodiments disclosed herein but the technical idea of the present invention is not limited thereto. It should be understood that all of variations, equivalents or substitutes contained in the concept and technical scope of the present invention are also included.

It will be understood that the terms "first" and "second" are used herein to describe various components but these components should not be limited by these terms. These terms are used only to distinguish one component from other components.

In this disclosure below, when one part (or element, device, etc.) is referred to as being 'connected' to another part (or element, device, etc.), it should be understood that the former can be 'directly connected' to the latter, or 'electrically connected' to the latter via an intervening part (or element, device, etc.). It will be further understood that when one component is referred to as being 'directly connected' or 'directly linked' to another component, it means that no intervening component is present.

The terms of a singular form may include plural forms unless they have a clearly different meaning in the context.

Additionally, in this specification, the meaning of "include," "comprise," "including," or "comprising," specifies a property, a region, a fixed number, a step, a process, an element and/or a component but does not exclude other properties, regions, fixed numbers, steps, processes, elements and/or components.

Mobile terminals described in this specification may include mobile phones, smartphones, laptop computers, terminals for digital broadcast, personal digital assistants (PDAs), portable multimedia players (PMPs), navigation systems, slate PCs, tablet PCs, ultrabooks, and wearable devices (for example, smartwatchs, smart glasses, and head mounted displays (HMDs)).

However, it is apparent to those skilled in the art that configurations according to embodiments of the present invention disclosed in this specification are applicable to stationary terminals such as digital TVs, desktop computers, and digital signage, except for the case applicable to only mobile terminals.

Figure 1B:
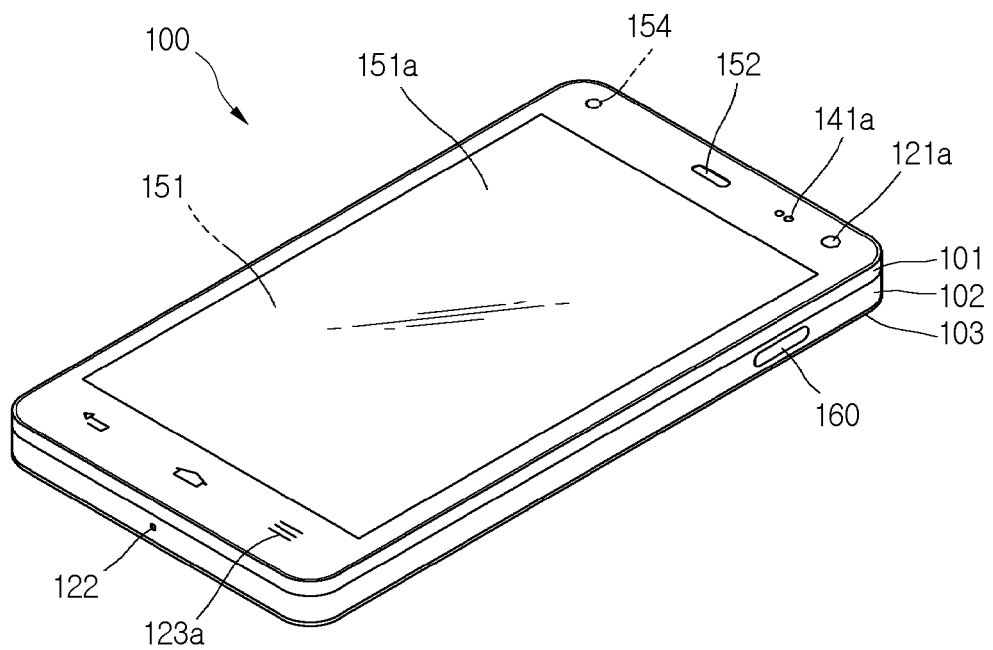
FIGS. 1B and 1C are views of a mobile terminal seen from different directions according to an embodiment of the present invention.
Figure 1C:
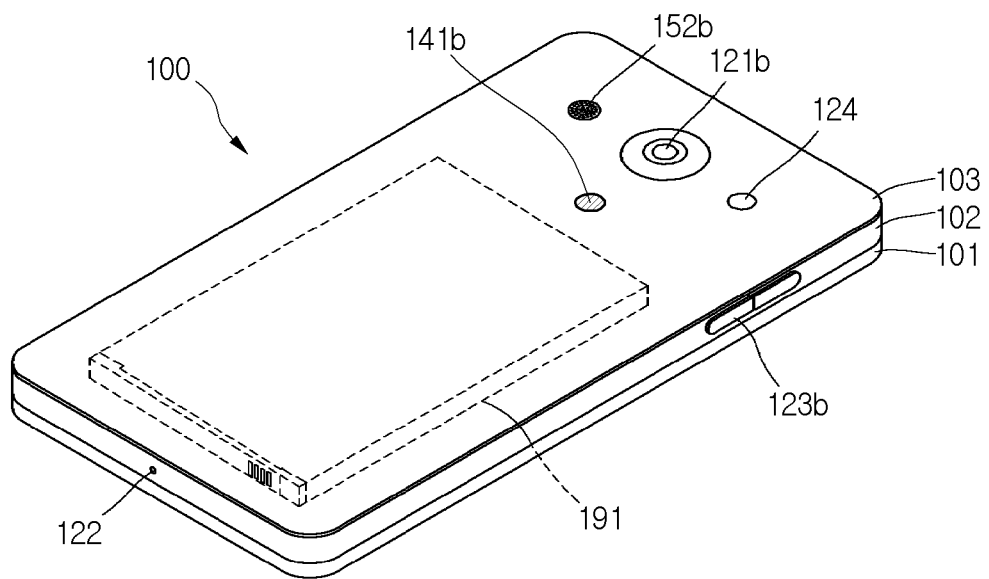

Referring to FIGS. 1A to 1C, FIG. 1A is a block diagram illustrating a mobile terminal according to an embodiment of the present invention. FIGS. 1B and 1C are views of a mobile terminal seen from different directions according to an embodiment of the present invention.

The mobile terminal 100 may include a wireless communication unit 110, an input unit 120, a sensing unit 140, an output unit 150, an interface unit 160, a memory 170, a control unit 180, and a power supply unit 190. In implementing a mobile terminal, components shown in FIG. 1A are not necessary, so that a mobile terminal described in this specification may include components less or more than the components listed above.

In more detail, the wireless communication unit 110 in the components may include at least one module allowing wireless communication between the mobile terminal 100 and a wireless communication system, between the mobile terminal 100 and another mobile terminal 100, or between the mobile terminal 100 and an external server. Additionally, the wireless communication unit 110 may include at least one module connecting the mobile terminal 100 to at least one network.

The wireless communication unit 110 may include at least one of a broadcast receiving module 111, a mobile communication module 112, a wireless internet module 113, a short-range communication module 114, and a location information module 115.

The input unit 120 may include a camera 121 or an image input unit for image signal input, a microphone 122 or an audio input unit for audio signal input, and a user input unit 123 (for example, a touch key and a mechanical key)) for receiving information from a user. Voice data or image data collected by the input unit 120 are analyzed and processed as a user's control command.

Then, the user input unit 123 may further include a back key 123a formed at the back case or back cover of a mobile terminal. At this point, a user may manipulate the back key 123a vertically or horizontally or may perform a press input by using the index or middle finger while grabbing a mobile terminal. The back key 123a may be formed of at least one physical key, screen, or sensor.

The sensing unit 140 may include at least one sensor for sensing at least one of information in a mobile terminal, environmental information around a mobile terminal, and user information. For example, the sensing unit 140 may include a proximity sensor 141, an acceleration sensor 142, and a gyro sensor 143. The proximity sensor 141 may include a front proximity sensor 141a and a back proximity sensor 141b. The front proximity sensor 141a is disposed at the front of the mobile terminal 100 and the back proximity sensor 141b is disposed at the back of the mobile terminal 100. The display unit 151 is disposed at the front of the mobile terminal 100.

Also, the sensing unit 140 may include at least one of an illumination sensor, a touch sensor, a magnetic sensor, a G-sensor, a gyroscope sensor, a motion sensor, an RGB sensor, an infrared (IR) sensor, a finger scan sensor, an ultrasonic sensor, an optical sensor (for example, the camera 121), a microphone 122, a battery gauge, an environmental sensor (for example, a barometer, a hygrometer, a thermometer, a radiation sensor, a thermal sensor, and a gas sensor), and a chemical sensor (for example, an electronic noise, a healthcare sensor, and a biometric sensor). Moreover, a mobile terminal disclosed in this specification may combines information sensed by at least two or more sensors among such sensors and may then utilize it.

The output unit 150 is used to generate a visual, auditory, or haptic output and may include at least one of a display unit 151, a sound output unit 152, a haptic module 153, and an optical output unit 154. The display unit 151 may be formed with a mutual layer structure with a touch sensor or formed integrally, so that a touch screen may be implemented. Such a touch screen may serve as the user input unit 123 providing an input interface between the mobile terminal 100 and a user and an output interface between the mobile terminal 100 and a user at the same time.

The interface unit 160 may serve as a path to various kinds of external devices connected to the mobile terminal 100. The interface unit 160 may include at least one of a wired/wireless headset port, an external charger port, a wired/wireless data port, a memory card port, a port connecting a device equipped with an identification module, an audio Input/Output (I/O) port, a video I/O port, and an earphone port. In correspondence to that an external device is connected to the interface unit 160, the mobile terminal 100 may perform an appropriate control relating to the connected external device.

Additionally, the memory 170 may store data supporting various functions of the mobile terminal 100. The memory 170 may store a plurality of application programs (for example, application programs or applications) running on the mobile terminal 100 and also data and commands for operations of the mobile terminal 100. At least part of such an application program may be downloaded from an external server through a wireless communication. Additionally, at least part of such an application program may be included in the mobile terminal 100 from the time of shipment in order to perform a basic function (for example, an incoming call, a transmission function, and a message reception) of the mobile terminal 100. Moreover, an application program may be stored in the memory 170 and installed on the mobile terminal 100, so that it may run to perform an operation (or a function) of the mobile terminal 100 by the control unit 180.

The control unit 180 may control overall operations of the mobile terminal 100 generally besides an operation relating to the application program. The control unit 180 may provide appropriate information or functions to a user or process them by processing signals, data, and information inputted/outputted through the above components or executing application programs stored in the memory 170.

Additionally, in order to execute an application program stored in the memory 170, the control unit 180 may control at least part of the components shown in FIG. 1A. Furthermore, in order to execute the application program, the control unit 180 may combine at least two of the components in the mobile terminal 100 and may then operate it.

The power supply unit 190 may receive external power or internal power under a control of the control unit 180 and may then supply power to each component in the mobile terminal 100. The power supply unit 190 includes a battery and the battery may be a built-in battery or a replaceable battery.

At least part of the each component may operate cooperatively in order to implement operations, controls, or control methods of a mobile terminal 100 according to various embodiments of the present invention described below. Additionally, the operations, controls, or control methods of a mobile terminal 100 may be implemented on the mobile terminal 100 by executing at least one application program stored in the memory 170.

Hereinafter, prior to examining various embodiments implemented through the mobile terminal 100, the above-listed components are described in more detail with reference to FIG. 1A.

First, in describing the wireless communication unit 110, the broadcast receiving module 111 of the wireless communication unit 110 may receive a broadcast signal and/or broadcast related information from an external broadcast management server through a broadcast channel. The broadcast channel may include a satellite channel and a terrestrial channel. At least two broadcast receiving modules for simultaneous broadcast reception for at least two broadcast channels or broadcast channel switching may be provided to the mobile terminal 100.

The mobile communication module 112 may transmit/receive a wireless signal to/from at least one of a base station, an external terminal, and a server on a mobile communication network established according to the technical standards or communication methods for mobile communication (for example, Global System for Mobile communication (GSM), Code Division Multi Access (CDMA), Code Division Multi Access 2000 (CDMA2000), Enhanced Voice-Data Optimized or Enhanced Voice-Data Only (EV-DO), Wideband CDMA (WCDMA), High Speed Downlink Packet Access (HSDPA), High Speed Uplink Packet Access (HSUPA), Long Term Evolution (LTE), and Long Term Evolution-Advanced (LTE-A)).

The wireless signal may include various types of data according to a voice call signal, a video call signal, or text/multimedia message transmission.

The wireless internet module 113 refers to a module for wireless internet access and may be built in or external to the mobile terminal 100. The wireless internet module 113 may be configured to transmit/receive a wireless signal in a communication network according to wireless internet technologies.

The wireless internet technology may include Wireless LAN (WLAN), Wireless-Fidelity (Wi-Fi), Wi-Fi Direct, Digital Living Network Alliance (DLNA), Wireless Broadband (WiBro), World Interoperability for Microwave Access (WiMAX), High Speed Downlink Packet Access (HSDPA), High Speed Uplink Packet Access (HSUPA), Long Term Evolution (LTE), and Long Term Evolution-Advanced (LTE-A) and the wireless internet module 113 transmits/receives data according at least one wireless internet technology including internet technology not listed above.

From the viewpoint that wireless internet access by WiBro, HSDPA, HSUPA, GSM, CDMA, WCDMA, LTE, and LTE-A is achieved through a mobile communication network, the wireless internet module 113 performing wireless internet access through the mobile communication network may be understood as one type of the mobile communication module 112.

The short-range communication module 114 may support Short-range communication by using at least one of Bluetooth™, Radio Frequency Identification (RFID), Infrared Data Association (IrDA), Ultra Wideband (UWB), ZigBee, Near Field Communication (NFC), Wireless-Fidelity Wi-Fi Direct, and Wireless Universal Serial Bus (USB) technologies. The short-range communication module 114 may support wireless communication between the mobile terminal 100 and a wireless communication system, between the mobile terminal 100 and another mobile terminal 100, or between networks including the mobile terminal 100 and another mobile terminal 100 (or an external server) through wireless area networks. The wireless area networks may be wireless personal area networks.

Here, the other mobile terminal 100 may be a wearable device (for example, a smart watch, a smart glass, and an HMD) that is capable of exchanging data (or interworking) with the mobile terminal 100. The short-range communication module 114 may detect (or recognize) a wearable device around the mobile terminal 100, which is capable of communicating with the mobile terminal 100 Furthermore, if the detected wearable device is a device authenticated to communicate with the mobile terminal 100, the control unit 180 may transmit at least part of data processed in the mobile terminal 100 to the wearable device through the short-range communication module 114. Accordingly, a user of the wearable device may use the data processed in the mobile terminal 100 through the wearable device. For example, according thereto, when a call is received by the mobile terminal 100, a user may perform a phone call through the wearable device or when a message is received by the mobile terminal 100, a user may check the received message.

The location information module 115 is a module for obtaining the location (or the current location) of a mobile terminal and its representative examples include a global positioning system (GPS) module or a Wi-Fi module. For example, the mobile terminal may obtain its position by using a signal transmitted from a GPS satellite through the GPS module. As another example, the mobile terminal may obtain its position on the basis of information of a wireless access point (AP) transmitting/receiving a wireless signal to/from the Wi-Fi module, through the Wi-Fi module. If necessary, the position information module 115 may perform a function of another module in the wireless communication unit 110 in order to obtain data on the location of the mobile terminal substitutionally or additionally. The location information module 115 is a module for obtaining the position (or the current position) of the mobile terminal and is not limited to a module directly calculating and obtaining the position of the mobile terminal.

Then, the input unit 120 is used for inputting image information (or signal), audio information (or signal), data, or information inputted from a user and the mobile terminal 100 may include at least one camera 121 in order for inputting image information. The camera 121 processes image frames such as a still image or a video obtained by an image sensor in a video call mode or a capturing mode. The processed image frame may be displayed on the display unit 151 or stored in the memory 170. Moreover, a plurality of cameras 121 equipped in the mobile terminal 100 may be arranged in a matrix structure and through the camera 121 having such a matrix structure, a plurality of image information having various angles or focuses may be inputted to the input terminal 100. Additionally, the plurality of cameras 121 may be arranged in a stereo structure to obtain the left and right images for implementing a three-dimensional image.

The microphone 122 processes external sound signals as electrical voice data. The processed voice data may be utilized variously according to a function (or an application program being executed) being performed in the mobile terminal 100. Moreover, various noise cancelling algorithms for removing noise occurring during the reception of external sound signals may be implemented in the microphone 122.

The user input unit 123 is to receive information from a user and when information is inputted through the user input unit 123, the control unit may control an operation of the mobile terminal 100 to correspond to the inputted information. The user input unit 123 may include a mechanical input means (or a mechanical key, for example, a button, a dome switch, a jog wheel, and a jog switch at the front, back or side of the mobile terminal 100) and a touch type input means. For example, the touch type input means may include a virtual key displayed on a touch screen through software processing, a soft key, a virtual key, or a touch key arranged at a portion other than the touch screen. Moreover, the virtual key or the visual key may be displayed on the touch screen in various forms and for example, may include graphic, text, icon, video, or a combination thereof.

Moreover, the sensing unit 140 may sense at least one of information in a mobile terminal, environmental information around a mobile terminal, and user information and may then generate a sensing signal corresponding thereto. On the basis of such a sensing signal, the control unit 180 may control the drive or control of the mobile terminal 100 or may perform data processing, functions, or operations relating to an application program installed in the mobile terminal 100. Representative sensors among various sensors included in the sensing unit 140 will be described in more detail.

First, the proximity sensor 141 refers to a sensor detecting whether there is an object approaching a predetermined detection surface or whether there is an object around by using the strength of an electromagnetic field or infrared, without mechanical contact. The proximity sensor 141 may disposed in an inner area of a mobile terminal surrounded by the touch screen or around the touch screen.

Examples of the proximity sensor 141 may include a transmission-type photoelectric sensor, a direct reflective-type photoelectric sensor, a mirror reflective-type photoelectric sensor, a high-frequency oscillation-type proximity sensor, a capacitive-type proximity sensors, a magnetic-type proximity sensor, and an infrared proximity sensor. If the touch screen is a capacitive type, the proximity sensor 141 may be configured to detect the proximity of an object by changes in an electric field according to the proximity of the object having conductivity. In this case, the touch screen (or a touch sensor) itself may be classified as a proximity sensor.

Then, according to this embodiment of the present invention, a back proximity sensor 141b in the proximity sensor 141 may determine the proximity of an object and also may detect a photoplethysmographic (PPG) signal. In this case, the back proximity sensor 141b may be called a heart rate sensor. For example, if the back proximity sensor 141b includes a light emitting unit emitting an IR signal or an LED signal and a light receiving unit receiving light reflected by a user's finger, it is possible to detect a user's heart rate from a signal of light detected by the light receiving unit.

When the light emitting unit of the back proximity sensor 141*b* emits light to a finger, blood, bone, and tissue absorb light and some of the light is reflected to be incident to the light receiving unit. Then, the light incident to the light receiving unit relates to skin, tissue, and an amount of blood and it is possible to detect a PPG signal by measuring a blood change due to a heart rate.

Moreover, for convenience of description, an action for recognizing the position of an object on the touch screen as the object is close to the touch screen without contacting the touch screen is called "proximity touch" and an action that the object actually contacts the touch screen is called "contact touch". A position that an object is proximity-touched on the touch screen is a position that the object vertically corresponds to the touch screen when the object is proximity-touched. The proximity sensor 141 may detect a proximity touch and a proximity touch pattern (for example, a proximity touch distance, a proximity touch direction, a proximity touch speed, a proximity touch time, a proximity touch position, and a proximity touch movement state). Moreover, the control unit 180 processes data (for information) corresponding to a proximity touch operation and a proximity touch pattern, detected through the proximity sensor 141, and furthermore, may output visual information corresponding to the processed data on the touch screen. Furthermore, according to whether a touch for the same point on the touch screen is a proximity touch or a contact touch, the control unit 180 may control the mobile terminal 100 to process different operations or data (or information).

The touch sensor detects a touch (or a touch input) applied to the touch screen (or the display unit 151) by using at least one of various touch methods, for example, a resistive film method, a capacitive method, an infrared method, an ultrasonic method, and a magnetic field method.

For example, the touch sensor may be configured to convert a pressure applied to a specific portion of the touch screen or changes in capacitance occurring at a specific portion into electrical input signals. The touch sensor may be configured to detect a position and area that a touch target applying a touch on the touch screen touches the touch sensor, a pressured when touched, and a capacitance when touched. Here, the touch target, as an object applying a touch on the touch sensor, may be a finger, a touch pen, a stylus pen, or a pointer, for example.

In such a manner, when there is a touch input on the touch sensor, signal(s) corresponding thereto are sent to a touch controller. The touch controller processes the signal(s) and then transmits corresponding data to the control unit 180. Therefore, the control unit 180 may recognize which area of the display unit 151 is touched. Herein, the touch controller may be an additional component separated from the control unit 180 or may be the control unit 180 itself.

Moreover, the control unit 180 may perform different controls or the same control according to types of a touch target touching the touch screen (or a touch key equipped separated from the touch screen). Whether to perform different controls or the same control according to types of a touch target may be determined according to a current operation state of the mobile terminal 100 or an application program in execution.

Moreover, the above-mentioned touch sensor and proximity sensor are provided separately or combined and may thus sense various types of touches, for example, short (or tap) touch), long touch, multi touch, drag touch, flick touch, pinch-in touch, pinch-out touch, swipe touch, and hovering touch for the touch screen.

The ultrasonic sensor may recognize position information of a detection target by using ultrasonic waves. Moreover, the control unit 180 may calculate the position of a wave source through information detected by an optical sensor and a plurality of ultrasonic sensors. The position of the wave source may be calculated by using the property that light is much faster than ultrasonic wave, that is, a time that light reaches an optical signal is much shorter than a time that ultrasonic wave reaches an ultrasonic sensor. In more detail, the position of the wave source may be calculated by using a time difference with a time that ultrasonic wave reaches by using light as a reference signal.

Moreover, the camera 121 described as a configuration of the input unit 120 may include at least one of a camera sensor (for example, CCD and CMOS), a photo sensor (or an image sensor), and a laser sensor.

The camera 121 and the laser sensor may be combined to detect a touch of a detection target for a three-dimensional image. The photo sensor may be stacked on a display device and is configured to scan a movement of a detection target close to the touch screen. In more detail, the photo sensor mounts a photo diode and a transistor (TR) in a row/column and scans content disposed on the photo sensor by using an electrical signal changing according to an amount of light applied to the photo diode. That is, the photo sensor may calculate the coordinates of a detection target according to the amount of change in light and through this, may obtain the position information of the detection target.

The display unit 151 may display (output) information processed in the mobile terminal 100. For example, the display unit 151 may display execution screen information of an application program running on the mobile terminal 100 or user interface (UI) and graphic user interface (GUI) information according to such execution screen information.

Additionally, the display unit 151 may be configured as a three-dimensional display unit displaying a three-dimensional image.

A three-dimensional display method, for example, a stereoscopic method (a glasses method), an autostereoscopic (no glasses method), a projection method (a holographic method) may be applied to the three-dimensional display unit The sound output unit 152 may output audio data received from the wireless communication unit 110 or stored in the memory 170 in a call signal reception or call mode, a recording mode, a voice recognition mode, or a broadcast reception mode. The sound output unit 152 may output a sound signal relating to a function (for example, a call signal reception sound and a message reception sound) performed by the mobile terminal 100. The sound output unit 152 may include a receiver, a speaker, and a buzzer.

The haptic module 153 generates various haptic effects that a user can feel. A representative example of a haptic effect that the haptic module 153 generates is vibration. The intensity and pattern of vibration generated by the haptic module 153 may be controlled by a user's selection or a setting of a control unit. For example, the haptic module 153 may synthesize and output different vibrations or output different vibrations sequentially.

The haptic module 153 may generate various haptic effects, for example, effects by a pin arrangement moving vertical to a contact skin surface, injection power or suction power of air through an injection port or a suction port, rubbing a skin surface, electrode contact, stimulus of electrostatic force and effects by the reproduction of cold/warm sense by using a device absorbing or emitting heat.

The haptic module 153 may be implemented to deliver a haptic effect through a direct contact and also allow a user to feel a haptic effect through a muscle sense such as a finger or an arm. The haptic module 153 may be more than two according to a configuration aspect of the mobile terminal 100.

The optical output unit 154 outputs a signal for notifying event occurrence by using light of a light source of the mobile terminal 100. An example of an event occurring in the mobile terminal 100 includes message reception, call signal reception, missed calls, alarm, schedule notification, e-mail reception, and information reception through an application.

A signal outputted from the optical output unit 154 is implemented as a mobile terminal emits single color of multi-color to the front or the back. The signal output may be terminated when a mobile terminal detects user's event confirmation.

The interface unit 160 may serve as a path to all external devices connected to the mobile terminal 100. The interface unit 160 may receive data from an external device, receive power and deliver it to each component in the mobile terminal 100, or transmit data in the mobile terminal 100 to an external device. For example, the interface unit 160 may include a wired/wireless headset port, an external charger port, a wired/wireless data port, a memory card port, a port connecting a device equipped with an identification module, an audio I/O port, a video I/O port, and an earphone port.

Moreover, the identification module, as a chip storing various information for authenticating usage authority of the mobile terminal 100, may include a user identity module (UIM), a subscriber identity module (SIM), and a universal subscriber identity module (USIM). A device equipped with an identification module (hereinafter referred to as an identification device) may be manufactured in a smart card form. Accordingly, the identification device may be connected to the terminal 100 through the interface unit 160.

Additionally, when the mobile terminal 100 is connected to an external cradle, the interface unit 160 may become a path through which power of the cradle is supplied to the mobile terminal 100 or a path through which various command signals inputted from the cradle are delivered to the mobile terminal 100 by a user. The various command signals or the power inputted from the cradle may operate as a signal for recognizing that the mobile terminal 100 is accurately mounted on the cradle.

The memory 170 may store a program for an operation of the control unit 180 and may temporarily store input/output data (for example, a phone book, a message, a still image, and a video). The memory 170 may store data on various patterns of vibrations and sounds outputted during a touch input on the touch screen.

The memory 170 may include at least one type of storage medium among flash memory type, hard disk type, Solid State Disk (SSD) type, Silicon Disk Drive (SDD) type, multimedia card micro type, card type memory (for example, SD or XD memory type), random access memory (RAM) type, static random access memory (SRAM) type, read-only memory (ROM) type, electrically erasable programmable read-only memory (EEPROM) type, programmable read-only memory (PROM) type, magnetic memory type, magnetic disk type, and optical disk type. The mobile terminal 100 may operate in relation to a web storage performing a storage function of the memory 170 on internet.

Moreover, as mentioned above, the control unit 180 may control operations relating to an application program and overall operations of the mobile terminal 100 in general. For example, if a state of the mobile terminal 100 satisfies set conditions, the control unit 180 may execute or release a lock state limiting an output of a control command of a user for applications.

Additionally, the control unit 180 may perform a control or processing relating to a voice call, data communication, and a video call may perform pattern recognition processing for recognizing handwriting input or drawing input on the touch screen as a text and an image, respectively. Furthermore, the control unit 180 may use at least one or a combination of the above components to perform a control in order to implement various embodiments described below on the mobile terminal 100.

The power supply unit 190 may receive external power or internal power under a control of the control unit 180 and may then supply power necessary for an operation of each component. The power supply unit 190 includes a battery. The battery is a rechargeable built-in battery and may be detachably coupled to a terminal body in order for charging.

Additionally, the power supply unit 190 may include a connection port and the connection port may be configured as one example of the interface unit 160 to which an external charger supplying power for charging of the battery is electrically connected.

As another example, the power supply unit 190 may be configured to charge a battery through a wireless method without using the connection port. In this case, the power supply unit 190 may receive power from an external wireless power transmission device through at least one of an inductive coupling method based on a magnetic induction phenomenon, and a magnetic resonance coupling method based on an electromagnetic resonance phenomenon.

Moreover, various embodiments below may be implemented in a computer or device similar thereto readable medium by using software, hardware, or a combination thereof.

Referring to FIGS. 1B and 1C, the disclosed mobile terminal 100 may have a bar-shaped terminal body. However, the present invention is not limited thereto and may be applied to various structures, for example, a watch type, a clip type, glass type, a folder type in which two or more bodies are coupled to be relatively movable, a flip type, a slide type, a swing type, and a swivel type. Descriptions relating to a specific type of a mobile terminal may be generally applied to another type of a mobile terminal.

Herein, as the mobile terminal 100 is regarded as an integrated one, the terminal body may be conceptually understood as referring to the mobile terminal 100.

The mobile terminal 100 may include a case (for example, a frame, a housing, and a cover) constituting an appearance. As shown in the drawing, the mobile terminal 100 may includes a front case 101 and a rear case 102. Various electronic components are disposed in an inner space formed by the coupling of the front case 101 and the rear case 102. At least one middle case is additionally disposed between the front case 101 and the rear case 102.

The display unit 151 is disposed at the front of the terminal body and outputs information. As shown in the drawing, a window 151a of the display unit 151 is mounted at the front case 101 to form the front of the terminal body together with the front case 101.

In some cases, an electronic component may be mounted at the rear case 102. Electronic components mountable on the rear case 102 may include a detachable battery, an identification module, and a memory card. In this case, a back cover 103 covering mounted electronic components may be detachably coupled to the rear case 102. Accordingly, when the back cover 103 is separated from the rear case 102, electronic components mounted at the rear case 102 are exposed to the outside.

Then, the back proximity sensor 141*b* may be formed at an additional position of the back of the terminal or formed together with another component or a button. As shown in FIG. 1C, the back proximity sensor 141*b* is additionally prepared at the back of the terminal but according to another embodiment of the present invention, the back proximity sensor 141*b* and a back key 123*a* may be prepared together.

As shown in the drawing, when the back cover 103 is coupled to the rear case 102, part of a side of the rear case 102 may be exposed to the outside. In some cases, during the coupling, the rear case 102 may be completely covered by the back cover 103. Moreover, an opening exposing the sound output unit 152*b* to the outside may be disposed at the back cover 103.

Such cases 101, 102, and 103 may be formed by injecting synthetic resin or may be formed of a metal, for example, stainless steel (STS), aluminum (Al), or titanium (Ti).

Unlike the example that a plurality of cases prepare an inner space receiving various components, the mobile terminal 100 may be configured to allow one case to prepare the inner space In this case, the mobile terminal 100 of a unibody where a synthetic resin or metal extends from the side to the back may be implemented.

Moreover, the mobile terminal 100 may include a waterproof unit (not shown) to prevent water from permeating the inside of the terminal body. For example, the waterproof unit may be disposed between the window 151*a* and the front case 101, between the front case 101 and the rear case 102, or between the rear case 102 and the back cover 103 and may include a waterproof member sealing the inner space when they are coupled to each other.

The mobile terminal 100 may include the display unit 151, the first and second sound output units 152*a* and 152*b*, the front proximity sensor 141*a*, the optical output unit 154, first and second cameras 121*a* and 121*b*, the first and second manipulation units 123*a* and 123*b*, the microphone 122, and the interface unit 160.

Hereinafter, as shown in FIGS. 1B and 1C, in relation to the mobile terminal 100, the display unit 151, the first sound output unit 152*a*, the front proximity sensor 141*a*, the optical output unit 154, the first camera 121*a*, and the first manipulation unit 123*a* are disposed at the front of the terminal body. The second manipulation unit 123*b*, the microphone 122, and the interface unit 160 are disposed at the side of the terminal body. The second sound output unit 152*b* and the second camera 121*b* are disposed at the back of the terminal body. This is described as one example.

However, such a configuration is not limited to such an arrangement. These configurations may be excluded or replaced or disposed at a different side, if necessary. For example, the first manipulation unit 123*a* may not be disposed at the front of the terminal body and the second sound output unit 152*b* may be disposed at the side of the terminal body instead of the back of the terminal body.

The display unit 151 may display (output) information processed in the mobile terminal 100. For example, the display unit 151 may display execution screen information of an application program running on the mobile terminal 100 or user interface (UI) and graphic user interface (GUI) information according to such execution screen information.

The display unit 151 may include at least one of a liquid crystal display (LCD), a thin film transistor-liquid crystal display (TFT LCD), an organic light-emitting diode (OLED), a flexible display, a 3D display, and an e-ink display.

Additionally, the display unit 151 may be more than two according to a configuration aspect of the mobile terminal 100. In this case, in the mobile terminal 100, a plurality of display units are disposed on one side, being spaced from each other or integrally, or may be disposed at different sides.

The display unit 151 may include a touch sensor detecting a touch on the display unit 151 in order to receive a control command through a touch method. When a touch is made on the display unit 151 by using this, the touch sensor may detect the touch and on the basis of this, the control unit 180 may generate a control command corresponding to the touch. A content inputted by a touch method may be a text or number, or an instruction in various modes, or a designation available menu item.

Moreover, the touch sensor may be configured in a film form having a touch pattern and thus, may be disposed between the window 151*a* and a display (not shown) on the back of the window 151*a* or may be a metal wire that is directly patterned on the back of the window 151*a*. Or, the touch sensor and the display may be formed integrally. For example, the touch sensor may be disposed on the substrate of the display or may be disposed inside the display.

In such a manner, both the display unit 151 and the touch sensor may form a touch screen and in this case, the touch screen may function as the user input unit 123 of FIG. 1A. In some cases, the touch screen may perform at least part of a function of the first manipulation unit 123*a*.

The first sound output unit 152*a* may be implemented as a receiver delivering a call sound to the ear of a user and the second sound output unit 152*b* may implemented as a loud speaker outputting various alarm sounds or a playback sound of multimedia.

A sound hole for emitting sound occurring from the first sound output unit 152*a* may be formed at the window 151*a* of the display unit 151. However, the present invention is not limited thereto and the sound may be configured to be emitted along an assembly gap (for example, a gap between the window 151*a* and the front case 101) between structures. In this case, a hole separately formed to output sound may not be seen or hidden in appearance so that the appearance of the mobile terminal 100 may become simpler.

The optical output unit 154 may be configured to emit light for notifying event occurrence. An example of an event includes message reception, call signal reception, missed calls, alarm, schedule notification, e-mail reception, and information reception through an application. The control unit 180 may control the optical output unit 154 to terminate an output of light once user's event confirmation is detected.

The camera 121*a* processes image frames such as a still image or a video obtained by an image sensor in a capturing mode or a video call mode. The processed image frame may be displayed on the display unit 151 or stored in the memory 170.

The first and second manipulation units 123*a* and 123*b*, as an example of the user input unit 123 manipulated to receive a command for controlling an operation of the mobile terminal 100, may be collectively known as a manipulation portion. The first and second manipulation units 123*a* and 123*b* may adopt any manner if it is in a tactile manner that a user manipulates touch, push, and scroll with tactile feeling. Additionally, the first and second manipulation units 123*a* and 123*b* may adopt a manner that a user manipulates proximity touch and hovering touch without tactile feeling.

In the drawing, the first manipulation unit 123a is a touch key exemplarily but the present invention is not limited thereto. For example, the first manipulation unit 123a may be a push key (i.e., a mechanical key) or a combination of a touch key and a push key.

Contents inputted by the first and second manipulation units 123a and 123b may be set variously. For example, the first manipulation unit 123a may receive a command, for example, menu, home key, cancel, and search and the second manipulation unit 123b may receive a command, for example, the volume adjustment of sound outputted from the first or second sound output unit 152a or 152b and switching to a touch recognition mode of the display unit 151.

Moreover, as another example of the user input unit 123, a back input unit (for example, a back key or a back button) may be disposed at the back of the terminal body. Such a back input unit is manipulated to receive a command for controlling an operation of the mobile terminal 100 and inputted contents may be set variously. For example, the back input unit may receive a command such as power on/off, start, end, and scroll or a command such as the volume adjustment of sound outputted from the first or second sound output unit 152a or 152b and switching to a touch recognition mode of the display unit 151. The back input unit may be implemented in a form in which a touch input, a push input, or a combination input thereof is available.

The back input unit may be disposed to overlap the front of the display unit 151 in a thickness direction of the terminal body. For example, when a user grabs the terminal body by one hand, the back input unit may be disposed at the back upper end part of the terminal body in order to allow manipulation by using the user's index finger. However, the present invention is not limited thereto and thus the position of the back input unit may vary.

In such a way, when the back input unit is equipped at the back of the terminal body, by using this, a new form of a user interface may be implemented. Additionally, when the above-described touch screen or back input unit are substituted for at least part of the first manipulation unit 123a equipped at the front of the terminal body and thus the first manipulation unit 123a is not disposed at the front of the terminal body, the display unit 151 may be configured with a larger sized screen.

Moreover, the mobile terminal 100 may include a fingerprint recognition sensor for recognizing the user's finger and the control unit 180 may use the fingerprint information detected through the fingerprint recognition sensor as an authentication means. The fingerprint recognition sensor may be built in the display unit 151 or the user input unit 123.

The microphone 122 may be configured to receive the user's voice or other sounds. The microphone 122 may be disposed at a plurality of positions and may be configured to receive stereo sound.

The interface unit 160 becomes a path to connect the mobile terminal 100 to an external device. For example, the interface unit 160 may be at least one of a connection terminal for connected to another device (for example, an earphone and an external speaker), a port for short-range communication (for example, IrDA Port, Bluetooth Port, and Wireless LAN Port), and a power supply terminal for supplying power to the mobile terminal 100. The interface 160 may be implemented in a socket form for receiving an external type card such a Subscriber Identification Module (SIM) card, a User Identity Module (UIM) card, and a memory card for storing information.

The second card 121b may be disposed at the back of the terminal body. In this case, the second camera 121b may have a substantially opposite capturing direction to the first camera 121a.

The second camera 121b may include a plurality of lenses arranged along at least one line. The plurality of lenses may be arranged in a matrix. Such a camera may be named as an array camera. When the second camera 121b is configured with an array camera, an image may be captured through various methods using a plurality of lenses and a better image quality may be obtained.

A flash 124 may be disposed adjacent to the second camera 121b. When the second camera 121b captures a subject, the flash 124 emits light toward the subject.

The second sound output unit 152b may be additionally disposed at the terminal body. The second sound output unit 152b may implement a stereo function together with the first sound output unit 152a and may be used to implement a speaker phone mode during a call.

At least one antenna for wireless communication may be equipped at the terminal body. An antenna may be built in the terminal body or may be formed at the case. For example, an antenna constituting part of the broadcast receiving module 111 of FIG. 1A may be configured to be withdrawn from the terminal body. Additionally, an antenna may be formed of a film type and attached to the inner side of the back cover 103 and a case including a conductive material may function as an antenna.

The power supply unit 190 of FIG. 1A for supplying power to the mobile terminal 100 is equipped at the terminal body. The power supply unit 190 may include a battery 191 built in the terminal body or detachable from the outside of the terminal body.

The battery 191 may be configured to receive power through a power cable connected to the interface unit 160. Additionally, the battery 191 may be configured to be charged wirelessly through a wireless charging device. The wireless charging may be implemented by a magnetic induction method or a resonance method (that is, a magnetic resonance method).

Moreover, as shown in the drawing, the back cover 103 is coupled to the rear case 102 to cover the battery 191 and this limits the withdrawal of the battery 191 and protects the battery 191 from external impact and foreign materials. When the battery 191 is configured to be detachable from the terminal body, the back cover 103 may be detachably coupled to the rear case 102.

An accessory for protecting the appearance or assisting or expanding a function of the mobile terminal 100 may be added to the mobile terminal 100. As an example of such an accessory, a cover or a pouch covering or receiving at least one side of the mobile terminal 100 may be provided. The cover or the pouch may interoperate with the display unit 151 and may be configured to expand a function of the mobile terminal 100. As another example of an accessory, a touch pen assisting or expanding a touch input for a touch screen may be provided.

Moreover, this present invention may display information processed in a mobile terminal by using a flexible display. Hereinafter, this will be described in more detail with reference to the accompanying drawings.

Figure 2:
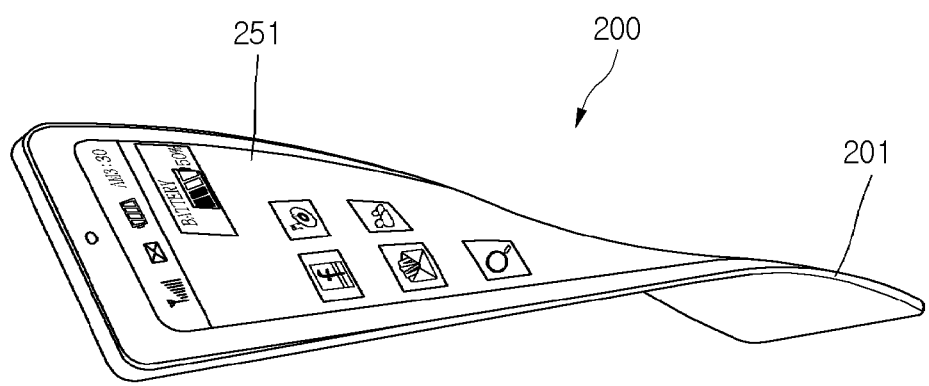
FIG. 2 is a conceptual diagram illustrating a mobile terminal according to another embodiment of the present invention.

FIG. 2 is a conceptual diagram illustrating a transformable mobile terminal 200 according to an embodiment of the present invention.

As shown in the drawing, a display unit 251 may be transformed by external force. The transformation may be at least one of warping, bending, folding, twisting, and curling of the display unit 251. Additionally, the transformable display unit 251 may be named as a flexible display. Herein, the flexible display unit 251 may include a general flexible display, an e-paper, and a combination thereof. In general, the mobile terminal 200 may have the same or similar features of the mobile terminal 100 shown in FIGS. 1A to 1C.

The general flexible display is a light and durable display maintaining the feature of an existing flat panel display and manufactured on a thin flexible substrate where warping, bending, folding, twisting, and curling are possible.

Additionally, the e-paper uses a display technique applying the feature of a general ink and is different from an existing flat panel display in that it uses reflected light. The e-paper may change information by using a twist ball or electrophoresis with a capsule.

When the flexible display unit 251 is not transformed (for example, a state having an infinite curvature radius, hereinafter referred to as a first state), the display area of the flexible display unit 251 becomes flat. When the flexible display unit 1 is transformed by external force (for example, a state having a finite curvature radius, hereinafter referred to as a second state), the display area of the flexible display unit 251 becomes a curved surface. As shown in the drawing, information displayed in the second state may be visual information outputted on the curved surface. Such visual information may be implemented by separately controlling the light emission of a sub-pixel disposed in a matrix. The sub-pixel means a minimum unit for implementing one color.

The flexible display unit 251 may be in a warping state (for example, a warping state vertically or horizontally) instead of a flat state during the first state. In this case, when external force is applied to the flexible display unit 251, the flexible display unit 251 may be transformed into a flat state (or a less warped state) or a more warped state.

Moreover, the flexible display unit 251 may be combined with a touch sensor to implement a flexible touch screen. When a touch is made on the flexible touch screen, the control unit 180 of FIG. 1A may perform a control corresponding to such a touch input. The flexible touch screen may be configured to detect a touch input in both the first state and the second state.

Moreover, the mobile terminal 200 according to a modified embodiment of the present invention may include a transformation detection means detecting the transformation of the flexible display unit 251. Such a transformation detection means may be included in the sensing unit 140 of FIG. 1A.

The transformation detection means may be equipped at the flexible display unit 251 or the case 201, so that it may detect information relating to the transformation of the flexible display unit 251. Herein, the information relating to transformation may include a direction that the flexible display unit 251 is transformed, the degree of transformation, a position that the flexible display unit 251 is transformed, a time that the flexible display unit 251 is transformed, and a restoring acceleration of the flexible display unit 251 and besides that, may include various information detectable due to the warping of the flexible display unit 251.

Additionally, on the basis of information relating to the transformation of the flexible display unit 251 detected by the transformation detection means, the control unit 180 may change the information displayed on the display unit 251 or may generate a control signal for controlling a function of the mobile terminal 200.

Moreover, the mobile terminal 200 according to a modified embodiment of the present invention may include a case 201 receiving the flexible display unit 251. The case 201 may be configured to be changed together with the flexible display unit 251 by external force in consideration of characteristics of the flexible display unit 251.

Furthermore, a battery (not shown) equipped in the mobile terminal 200 may be configured to be changed together with the flexible display unit 251 by external force in consideration of characteristics of the flexible display unit 251. In order to implement the battery, a stack and folding method stacking up battery cells may be applied.

A state of the transformed flexible display unit 251 is not limited to external force. For example, when the flexible display unit 251 has the first state, it changes into the second state by a command of a user or an application.

Then, a proximity sensor may be formed at each of the front and back of such a flexible terminal and such proximity sensors may sense the proximity of an object and also may sense the user's heart rate.

Moreover, a mobile terminal may expand to a wearable device that can be worn on the body beyond the level that a user mainly grabs the mobile terminal by a hand. Such a wearable device may include a smart watch, a smart glass, and an HMD. Hereinafter, examples of a mobile terminal expanding to a wearable device are described.

The wearable device may exchange data (or interoperate) with another mobile terminal 100. The short-range communication module 114 may detect (or recognize) a wearable device around the mobile terminal 100, which is capable of communicating with the mobile terminal 100 Furthermore, if the detected wearable device is a device authenticated to communicate with the mobile terminal 100, the control unit 180 may transmit at least part of data processed in the mobile terminal 100 to the wearable device through the short-range communication module 114. Accordingly, a user may use the data processed in the mobile terminal 100 through the wearable device. For example, when a call is received by the mobile terminal 100, a user may perform a phone call through the wearable device or when a message is received by the mobile terminal 100, a user may check the received message.

Figure 3:
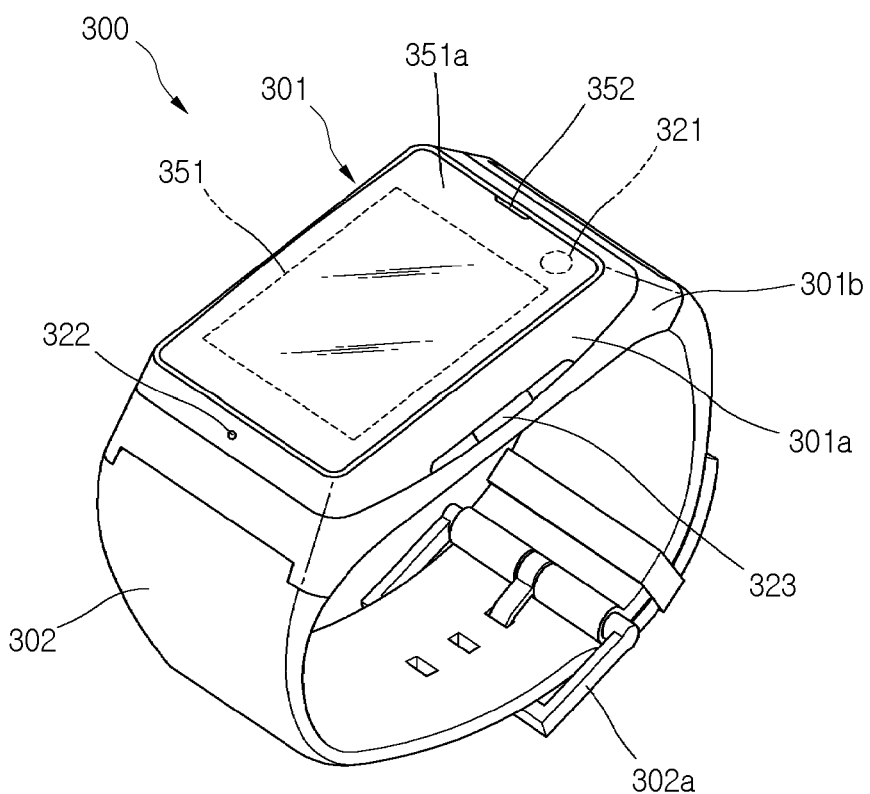
FIG. 3 is a perspective view illustrating a watch type mobile terminal according to another embodiment of the present invention.

FIG. 3 is a perspective view illustrating a watch type mobile terminal 300 according to another embodiment of the present invention.

Referring to FIG. 3, the watch type mobile terminal 300 includes a body 301 including a display unit 351 and a band 302 connected to the body 301 to be worn on a wrist. In general, the mobile terminal 300 may have the same or similar features of the mobile terminal 100 shown in FIGS. 1A to 1C.

The body 301 includes a case forming the appearance. As shown in the drawings, the case includes a first case 301a and a second case 301b preparing an inner space that receives various electronic components. However, the present invention is not limited thereto and one case may be configured to prepare the inner space so that the unibody mobile terminal 300 may be implemented.

The watch type mobile terminal 300 may be configured to allow wireless communication and an antenna for the wireless communication may be installed at the body 301. Moreover, the antenna may expand its performance by using a case. For example, a case including a conductive material is electrically connected to an antenna to expand a ground area or a radiation area.

The display unit 351 is disposed at the front of the body 301 to output information and a touch sensor is equipped at the display unit 351 to be implemented as a touch screen. As shown in the drawing, a window 351a of the display unit 351 is mounted at the first case 301a to form the front of the terminal body together with the first case 301a.

The body 301 may include a sound output unit 352, a camera 321, a microphone 322, and a user input unit 323. When the display unit 351 is implemented as a touch screen, it may function as the user input unit 323 and accordingly, there is no additional key at the body 301.

The band 302 is worn on the wrist to surround it and may be formed of a flexible material in order for easy wearing. As such an example, the band 302 may be formed of leather, rubber, silicon, and synthetic resin. Additionally, the band 302 may be configured to be detachable from the body 301, so that it may be replaced with various forms of bands according to user preferences.

Moreover, the band 302 may be used to expand the performance of an antenna. For example, an antenna is electrically connected to a band so that a ground expansion unit (not shown) expanding a ground area may be built in.

The band 302 may include a fastener 302a. The fastener 302a may be implemented by a buckle, a snap-fit available hook structure, or velcro (a brand name) and may include a stretchable interval or material. This drawing illustrates an example that the fastener 302a is implemented in a buckle form.

Then, a proximity sensor may be formed at each of the front and back of such a watch type mobile terminal and such proximity sensors may sense the proximity of an object and also may sense the user's heart rate.

Figure 4:
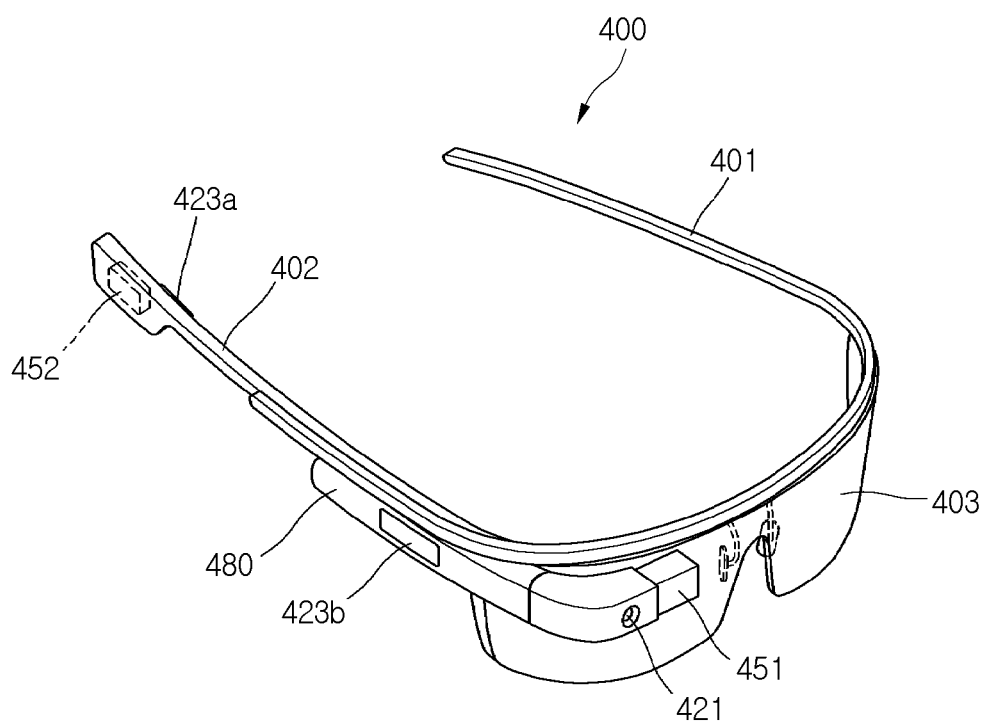
FIG. 4 is a perspective view illustrating a glass type mobile terminal according to another embodiment of the present invention.

FIG. 4 is a perspective view illustrating a glass type mobile terminal 400 according to another embodiment of the present invention.

The glass type mobile terminal 400 may be configured to be worn on the head portion of a human body and for this, may include a frame part (for example, a case and a housing). The frame part may be formed of a flexible material in order for each wearing. In this drawing, the frame part includes a first frame 401 and a second frame 402 formed of different materials. In general, the mobile terminal 400 may have the same or similar features of the mobile terminal 100 shown in FIGS. 1A to 1C.

The frame part is supported by the head portion and provides a space for mounting various components. As shown in the drawing, electronic components such as a control module 480 and a sound output module 452 may be mounted at the frame part. Additionally, a lens 403 covering at least one of the left eye and the right eye may be detachably mounted at the frame part.

The control module 480 may be configured to control various electronic components equipped at the mobile terminal 400. The control module 480 may be understood as a component corresponding to the above-described control unit 180. In this drawing, the control module 480 is installed at the frame part on one side of the head portion. However, the position of the control module 480 is not limited thereto.

The display unit 451 may be implemented in an HMD form. The HMD form refers to a display method for displaying an image directly in front of the user's eyes. When a user wears a glass type mobile terminal 400, in order to provide an image directly in front of the user's eyes, the display unit 451 may be disposed in correspondence to at least one of the left eye and the right eye. In this drawing, in order to output an image toward the user's right eye, the display unit 451 is disposed in correspondence to a portion corresponding to the right eye.

The display unit 451 may project an image to the user's eye by using a prism. Additionally, in order to allow a user to see the projected image and a general front view (that is, a range that the user can see through the eyes), the prism may be transparent.

In such a way, an image outputted through the display unit 451 may be overlapped with a general view and displayed. The mobile terminal 400 may provide augmented reality (AR) superimposing a virtual image on a real image or a background and displaying it as one image by using characteristics of such a display.

The camera 421 is disposed adjacent to at least one of the left eye and the right eye to capture a front image. Since the camera 421 is disposed adjacent to the eye, it may obtain an image of a scene that a user sees.

In this drawing, the camera 421 is equipped at the control module 480 but the present invention is not limited thereto. The camera 421 may be installed at the frame part and may be provided in plurality to obtain a three-dimensional image.

The glass type mobile terminal 400 may include user input units 423a and 423b manipulated to receive a control command. The user input units 423a and 423b may adopt any method if it is a tactile manner that a user manipulates touch and push with tactile feeling. In this drawing, the user input units 423a and 423b of a push and touch input method are equipped at the frame part and the control module 480, respectively.

Additionally, the glass type mobile terminal 400 may include a microphone (not shown) receiving sound and processing it electrical voice data and a sound output module 452 outputting sound. The sound output module 452 may be configured to deliver sound through a general sound output method or a bone conduction method. When the sound output module 452 is implemented with a bone conduction and a user wears the mobile terminal 400, the sound output module 342 closely contacts the head portion and delivers sound by vibrating the skull.

Then, a proximity sensor may be formed at the front or back of such a glass type mobile terminal or at a portion contacting the human face and such proximity sensors may sense the proximity of an object and also may sense the user's heart rate.

Hereinafter, embodiments relating to a control method implemented in such a configured mobile terminal are described with reference to the accompanying drawings. It is apparent to those skilled in the art that the present invention may be specified in a different specific form without departing from the scope and essential features of the present invention.

Figure 5:
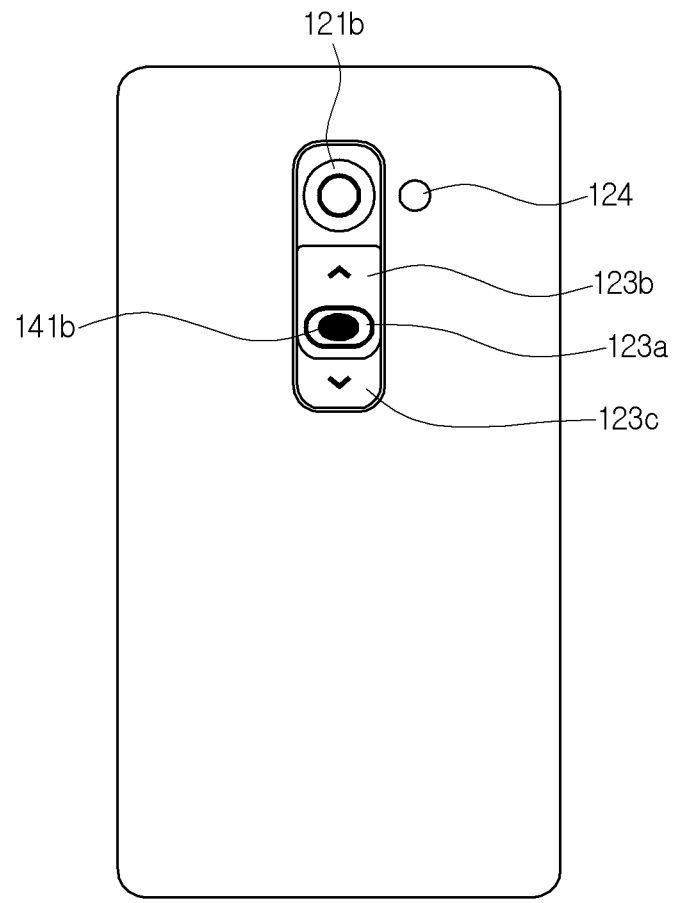
FIG. 5 is a view when a user input unit is formed at the back of a mobile terminal according to an embodiment of the present invention.

FIG. 5 is a view when a user input unit is formed at the back of a mobile terminal according to an embodiment of the present invention.

Referring to FIG. 5, a camera 121, a flash 124, at least one back key 131a, and a back proximity sensor 141b may be disposed at the back of the mobile terminal 100.

The at least one back physical key 131a may include an up key, an OK key, a power key, or a down key and if the physical key 131a is implemented as a power key, besides the power key, as shown in FIG. 5, an up key 123b and a down key 123c may be further formed.

Then, the back proximity sensor 141b may be formed together with one of the at least one back physical key 131a and for example, a back proximity sensor may be formed at the power key 123a.

One or more back keys 131a, 131b, and 131c may serves as at least one soft key in a soft key area. For example, the back keys 131a, 131b, and 131c may serves as a plurality of soft keys. Moreover, a combination of the back keys 131a, 131b, and 131c may serves as a plurality of soft keys.

Then, a structure of the back proximity sensor 141b according to an embodiment of the present invention will be described with reference to FIGS. 6 and 7.

Figure 6:
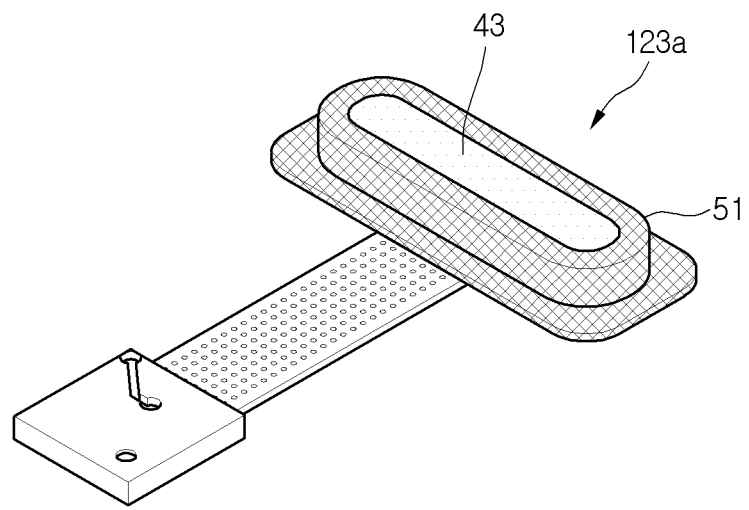
FIG. 6 is a view illustrating an appearance of a back key including a back proximity sensor according to an embodiment of the present invention.

FIG. 6 is a view illustrating an appearance of a back key including a back proximity sensor according to an embodiment of the present invention.

As shown in FIG. 6, the back key 123a may be an OK key or a power key at the terminal back and in this case, a user may deliver a user command to a terminal by pressing the back key 123a. Then, the back key 123a may has a body 51 forming the appearance and part of the upper surface of the body 51 has a window formed of a material transmitting light. The material transmitting light may be formed of glass, for example, and in this case, part of the upper surface of the body 51 may be formed of a front glass 43. The front glass 43 occupies part of the back key 123a.

A configuration of a back proximity sensor formed in the front glass 43 and detecting whether an object approaches and a PPG signal from a human body (for example, a finger) will be described with reference to FIG. 7.

Figure 7:
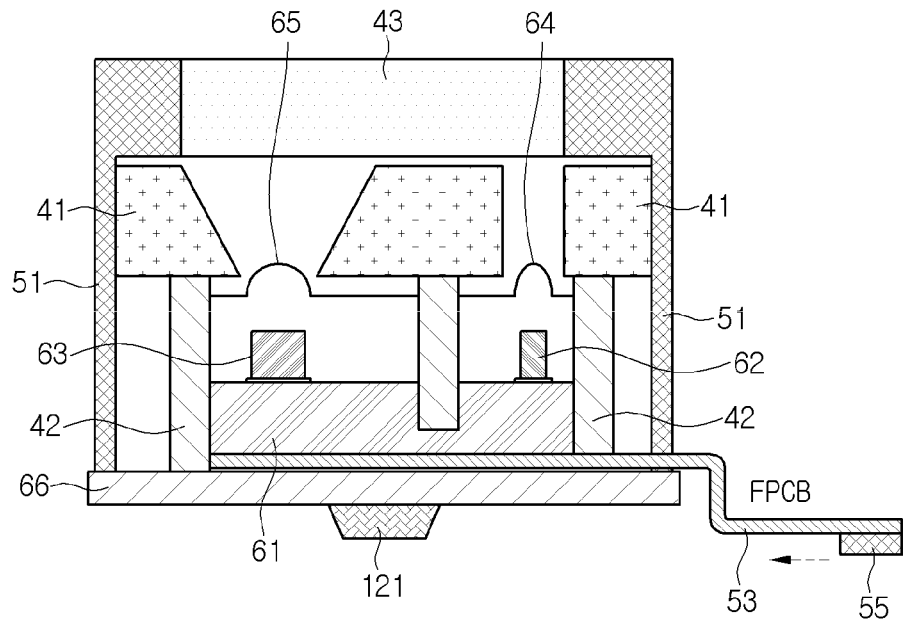
FIG. 7 is a view illustrating a sectional configuration of a back key including a back proximity sensor according to an embodiment of the present invention.

FIG. 7 is a view illustrating a sectional configuration of a back key including a back proximity sensor according to an embodiment of the present invention.

Referring to FIG. 7, the back key 123a including the back proximity sensor 141b includes a body 51, a flexible printed circuit board (FPCB) 53 for transmitting a detect signal of the back proximity sensor 141b, a back proximity sensor of the back physical key 131, and a connector 55 supporting an electrical connection between the back proximity sensor 141b and the mobile terminal 100.

Additionally, the back physical key 131 including the back proximity sensor 141b includes a shock absorbing material 41, a partition wall 42, a front glass 43, a body 51, an FPCB 53, a connector 55, a first substrate 61, a light emitting device 62, a light receiving unit 63, a first convex lens 64, a second convex lens (65), and a second substrate 66.

The light emitting device 62 and the light receiving device 63 are mounted on the first substrate 61, and the light emitting device 62 is mounted on the first substrate 61 and emits light for check a proximity state of an object. Then, the light emitting device 62 may emit infrared light or LED light.

The light receiving device 63 is mounted on the first substrate 61, receives reflected light obtained when light emitted from the light emitting device 62 is reflected by an object, and then generates a signal according to the intensity of the received light. Then, the light receiving device 63 includes an infrared illumination sensor or a photo diode and detects the illumination of light by receiving the light. Then, a signal received in such a manner may be used to check whether an object approaches and the user's heart rate through the control unit 180.

The partition wall 42 generates a path of light emitted by the light emitting device 32 and a path of light received by the light receiving device 33.

The shock absorbing material 41 may prevent the changes in distance between the front glass 43 and the light emitting device 62 or distance between the front glass 43 and the light receiving device 63, by a continuous pressure applied to the front glass 43.

The first convex lens 64 is disposed at the upper part of the light emitting device 62 and improves the straightness of infrared emitted from the light emitting device 62.

The second convex lens 65 is disposed at the upper part of the light receiving device 63 and condenses a reflected light obtained when light emitted from the light emitting device 62 is reflected by an object on the light receiving device 63.

The partition wall 42, the first substrate 61, the light emitting device 62, the light receiving device 63, the first convex lens 64, and the second convex lens 65 may form an assembly of the back proximity sensor 141b.

The second substrate 66 mounts the assembly of the front proximity sensor 141b and the FPCB 53.

The back key and the back proximity sensor having such a configuration may determine whether an object approaches and when a human body maintains a fixed position for a predetermined time at the top of the light emitting device 62 and the light receiving device 63, the control unit 180 may obtain a PPG signal from an optical signal received through the light receiving device 63 so as to check the heart rate. Then, when light generated from the light emitting device 62 is reflected by an object and then is incident to the light receiving device 63, it is possible to identify the color of an object close to the back proximity sensor or the back key.

Figure 8:
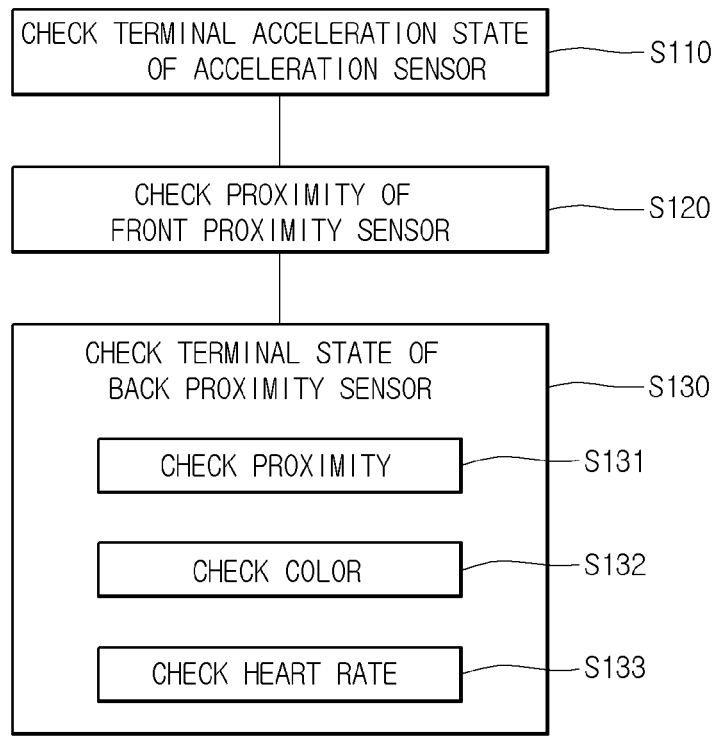
FIG. 8 is a view illustrating a method of obtaining state information of a mobile terminal according to an embodiment of the present invention.

FIG. 8 is a view illustrating a method of obtaining state information of a mobile terminal according to an embodiment of the present invention.

Herein, the state information of the mobile terminal includes information through which the control unit 180 determines a state that a current mobile terminal is positioned, a state that a mobile terminal s manipulated, or a state that a mobile terminal moves by using at least one sensor.

Operation S110 to operation S130 are shown in FIG. 8 but theses operations are not shown in order. Thus, their order may vary.

First, the control unit 180 may check an acceleration state of a terminal by using an acceleration sensor in operation S110. That is, the control unit 180 may check whether the terminal is disposed at a fixed position from a shaking state of the terminal sensed by the acceleration sensor 142.

Then, the control unit 180 may check whether a subject (or an object) approaches the terminal front by using the front proximity sensor 141a in operation S120. When the degree of proximity detected by the front proximity sensor 141a is greater than a reference value, the control unit 180 may determine a proximity detection state as a FAR state. When the degree of proximity detected by the front proximity sensor 141a is less than a reference value, the control unit 180 may determine a proximity detection state as a NEAR state.

Then, the control unit 180 may check state information of the terminal by using the back proximity sensor 141b in operation S130.

In more detail, the control unit 180 may check a state of the terminal in addition to whether an object approaches at the back in operation S131. When the degree of proximity detected by the back proximity sensor 141b is greater than a reference value, the control unit 180 may determine a proximity detection state as a FAR state. When the degree of proximity detected by the back proximity sensor 141b is less than a reference value, the control unit 180 may determine a proximity detection state as a NEAR state.

Additionally, the control unit 180 may check the color of a closely located object by using the back proximity sensor 141b in operation S132.

Even when the light emitting device 62 and the light receiving device 63 related to infrared, since the reflectivity of infrared varies according to the color of an object, color may be identified through a proximity sensor. For example, the number of identified colors may be four or eight.

Additionally, the control unit 180 may check a photoplethysmographic (PPG) detection state of the back proximity sensor 141b in operation S133. That is, the control unit 180 may check the user's heart rate by using the back proximity sensor 141b. Since the back proximity sensor 141b includes the light emitting device 62 and the light receiving device 63, it may operate as a PPG sensor detecting a PPG signal. According to an embodiment of the present invention, it is described that a PPG signal is detected by using the back proximity sensor 141b but when a front proximity sensor is formed as shown in FIG. 7, it is possible to detect a PPG signal of a human body by using a front proximity sensor.

The control unit 180 may detect a state in which the mobile terminal 100 is placed spatially on the basis of at least one of the presence of a predetermined shaking pattern, a proximity detection state of the front proximity sensor 141a, a proximity detection state of the back proximity sensor 141b, a color detection state of the back proximity sensor 141b, and a PPG signal detection state of the back proximity sensor 141b.

Hereinafter, several examples of state information of a mobile terminal that the control unit 180 is able to determine are listed.

State Information of Terminal 1

When an acceleration pattern is shaken, a front proximity sensor is checked as FAR, a back proximity sensor is checked as NEAR, and a PPG signal is checked through the back proximity sensor, the control unit 180 determines that a user grabs a terminal. Then, it is determined that the intention of a user is to check the heart rate.

Then, when the color of an object checked by a back proximity sensor instead of the PPG signal is the color of a hand, the control unit 180 may determine that a user grabs the terminal.

State Information of Terminal 2

When an acceleration pattern is shaken, a front proximity sensor is checked as FAR, a back proximity sensor is checked as NEAR, and a color detected by the back proximity sensor is not the color of a hand, the control unit 180 determines that a terminal is placed inside a started car. In this case, the control unit 180 may further check that there is no PPG signal through the back proximity sensor.

State Information of Terminal 3

When an acceleration pattern is shaken, a front proximity sensor is checked as NEAR, a back proximity sensor is checked as NEAR, and a color detected by the back proximity sensor is the color of a hand, the control unit 180 determines that a user moves a terminal closer to the ear while grabbing the terminal by a hand.

In this case, the control unit 180 may determined that a user is making a phone call and has an intention to make a phone call and may control the terminal to operate in a call mode in addition to turning off the screen of the display unit 151. Then, the control unit 180 may further perform an operation such as volume adjustment when a movement of an object (for example, a finger) is checked by the front proximity sensor.

State Information of Terminal 4

When an acceleration pattern is shaken, a front proximity sensor and a back proximity sensor are checked as NEAR, and a color detected by the back proximity sensor is not the color of a hand, the control unit 180 determines that a terminal is located in a moving closed space. Herein, the closed space may be a space where both the front proximity sensor and the back proximity sensor detect a NEAR state as in a bag or a pocket.

In this case, the control unit 180 may control a sound or haptic output of the terminal to be greater than a value set by a user, turn off the screen of the display unit, or, contrary to this, control the screen to be brighter.

State Information of Terminal 5

When an acceleration pattern is shaken, a front proximity sensor is checked as NEAR, a back proximity sensor is checked as FAR, and a color detected by the back proximity sensor is not the color of a hand, the control unit 180 determines that a user moves a terminal closer to the ear while grabbing the terminal by a hand but the user's finger is not located on a back key or the back proximity sensor.

In this case, the control unit 180 determines that a user does not intend to deliver the user's own heart rate to others (for example, the other part of a phone call). Then, the control unit 180 determines that the user has an intention to turn off an operation of the terminal by using the heart rate information.

State Information of Terminal 6

When an acceleration pattern is shaken, a front proximity sensor and a back proximity sensor are checked as FAR, and a color detected by the back proximity sensor is the color of a hand, the control unit 180 determines that a user grabs a terminal by a hand but the finger of the user does not sufficiently contact the back proximity sensor to measure a heart rate. That is, it is determined that the user's finger is spaced a predetermined distance apart from the front glass of the back proximity sensor.

In this case, the control unit 180 may allow a terminal to perform a specific operation according to a movement of an object (for example, a finger) measured through the back proximity sensor. For example, when a movement of a finger is detected by the back proximity sensor, the control unit 180 may control operations, for example, adjusting the sound volume of a terminal, releasing a lock state when the terminal is in the lock state, or starting capturing an image when a camera application operates.

State Information of Terminal 7

When an acceleration pattern is not shaken, a front proximity sensor and a back proximity sensor are checked as NEAR, and a color detected by the back proximity sensor is not the color of a hand, the control unit 180 determines that a terminal is located in a fixed closed space.

State Information of Terminal 8

When an acceleration pattern is not shaken, a front proximity sensor is checked as NEAR, a back proximity sensor is checked as FAR, and a color detected by the back proximity sensor is a color other than the color of a hand, the control unit 180 determines that a terminal is disposed at a table or a cradle while the screen of the terminal is toward the bottom.

In this case, the control unit 180 may more specifically determine state information of the terminal by using tilt information detected through a gyro sensor 143. For example, while State Information of Terminal 8 is checked, if the tilt check result of the terminal is parallel to the ground, it is determined the screen of the terminal is toward the bottom and is disposed at an object such as a table. Then, if the slope check result of the terminal is not parallel to the ground, it is determined that the screen of the terminal is toward a cradle and is fixed at the cradle.

Then, through such information, the control unit 180 determines whether the terminal is placed at a table such as a dining table and a desk in a household or whether the terminal is placed in a car that does not start yet.

State Information of Terminal 9

When an acceleration pattern is not shaken, a front proximity sensor is checked as FAR, a back proximity sensor is checked as NEAR, and a color detected by the back proximity sensor is a color other than the color of a hand, the control unit 180 determines that a terminal is disposed at a table or a cradle while the screen of the terminal is toward the top. Then, like using the sensing result of the gyro sensor 143 in State Information of Terminal 8, the control unit 180 may determine whether the terminal is placed at a table according to the tilt of the terminal or whether the terminal is slantly fixed at an object such as a cradle.

Then, through such information, the control unit 180 determines whether the terminal is placed at a table such as a dining table and a desk in a household or whether the terminal is placed in a car that does not start yet.

State Information of Terminal 10

When an acceleration pattern is not shaken, a front proximity sensor and a back proximity sensor are checked as FAR, and a color detected by the back proximity sensor is a color other than the color of a hand, when the tilt measured by a gyro sensor is not parallel to the ground, the control unit 180 determines that a terminal is slantly fixed at a object such as a cradle.

Then, through such information, the control unit 180 determines whether the terminal is placed at a table such as a dining table and a desk in a household or whether the terminal is placed in a car that does not start yet.

State Information of Terminal 11

When a movement of a terminal is greater than a first reference value and less than a second reference value according to an acceleration sensor, the control unit 180 may determine that a user is walking.

In this case, when it is determined that a certain object approaches by using a back proximity sensor of a terminal, the control unit 180 warns of danger through a screen or generates vibration, so that it prevents bumping into an approaching object while a user walks and manipulates a terminal.

Then, when a PPG signal is detected through the back proximity sensor, the control unit 180 may monitor the heart rate while a user is walking or may provide medical service using the measured heart rate.

State Information of Terminal 12

When a movement of a terminal is greater than a second reference value according to an acceleration sensor, the control unit 180 may determine that a user is running. At this point, like State Information of Terminal 11, the control unit 180 may inform the danger of an object approaching closer to a user.

Then, when a PPG signal is detected through the back proximity sensor, the control unit 180 may monitor whether the heart rate becomes greater than a predetermined value and may warn of danger to a user.

Figure 9:
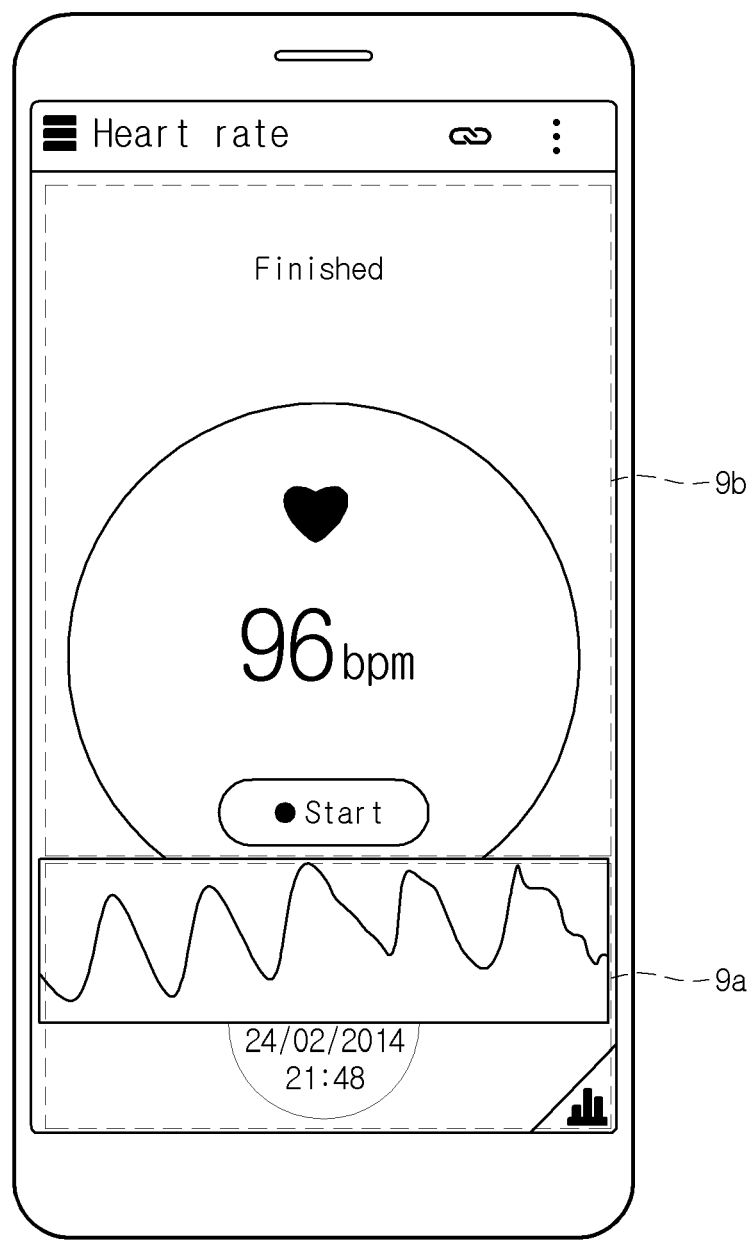
FIG. 9 is a view when information on a measured heart rate is displayed on a screen of a terminal according to an embodiment of the present invention.

FIG. 9 is a view when information on a measured heart rate is displayed on a screen of a terminal according to an embodiment of the present invention.

When the user's heart rage is measured by a back proximity sensor prepared at a back key or a heart rate sensor separately prepared at a terminal, heart rate information may be displayed on a screen.

Referring to FIG. 9, the screen includes a heart rate information area 9b where a heart rate is displayed and a heart rate area 9a where a graph of a measured PPG signal is displayed. Also, a user may re-measure a heart rate by touching the heart rate information are 9b and the heart rate graph area 9a or may check a previous heart rate measurement result.

Additionally, in this embodiment, when a user positions the finger at a heart rate sensor, that is, a back proximity sensor, information on a finger position for accurate heat rate measurement may be displayed. This will be described with reference to FIGS. 10 and 11.

Figure 10A:
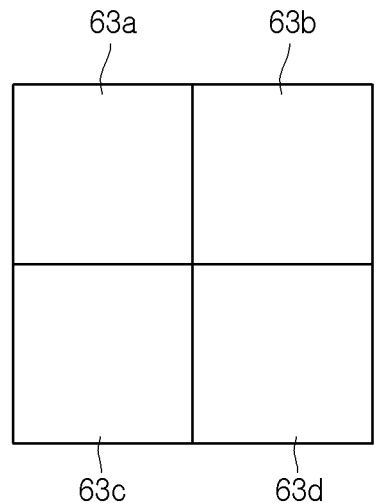
FIGS. 10A to 10C are views illustrating a configuration of a light receiving device for measuring a heart rate according to an embodiment of the present invention.
Figure 10B:
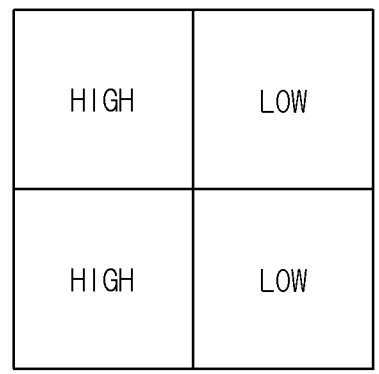
Figure 10C:
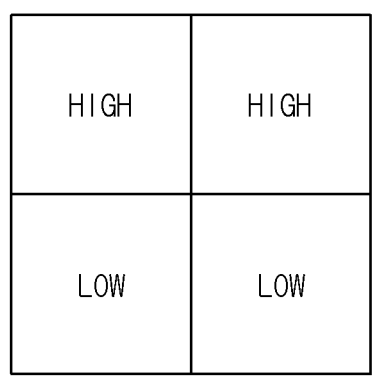

FIGS. 10A to 10C are views illustrating a configuration of a light receiving device for heart rate measurement according to an embodiment of the present invention. FIGS. 11A to 11D are views illustrating a UI guiding the position of a user's finger according to an embodiment of the present invention.

First, referring to FIGS. 10A to 10O, a light receiving device 63 may be configured with a plurality of photo diodes. In this case, when the finger of a user deviates from the reference position, an amount of light received by the photo diodes may vary.

As shown in FIG. 10B, when an amount of light received through a first photo diode 63a and a third photo diode 63c in the light receiving device 63 is large and an amount of light received through a second photo diode 63b and a fourth photo diode 63d is relatively small, the user's finger is biased to the left.

Then, as shown in FIG. 10O, when an amount of light received through a first photo diode 63a and a third photo diode 63c in the light receiving device 63 is large and an amount of light received through a second photo diode 63b and a fourth photo diode 63d is relatively small, the user's finger is biased to the left.

Figure 11A:
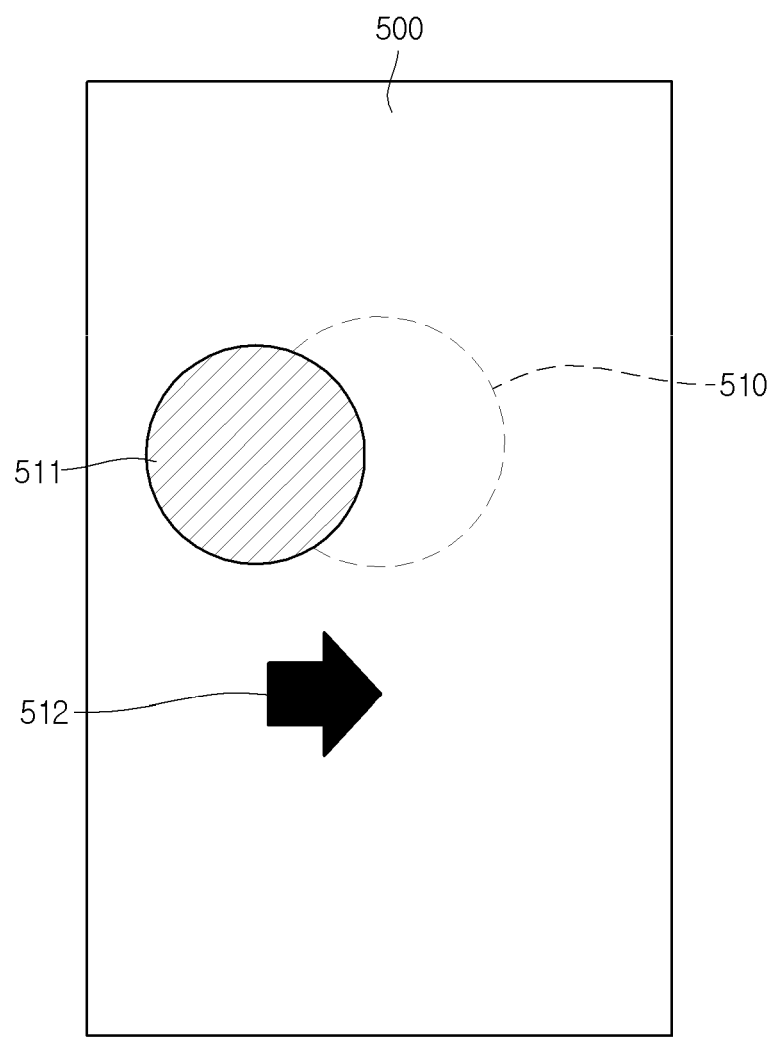
FIGS. 11A to 11D are views illustrating a UI for guiding the position of a user finger according to an embodiment of the present invention.

At this point, the control unit 180 may display a reference position image 510 notifying the position of a desired finger and a current position image 511 on a screen 500 of a display unit. Then, as shown in FIG. 10B, when the user's finger is biased to the left, as shown in FIG. 11A, a guide image 512 inducing the finger to move to the right may be displayed together.

Figure 11B:
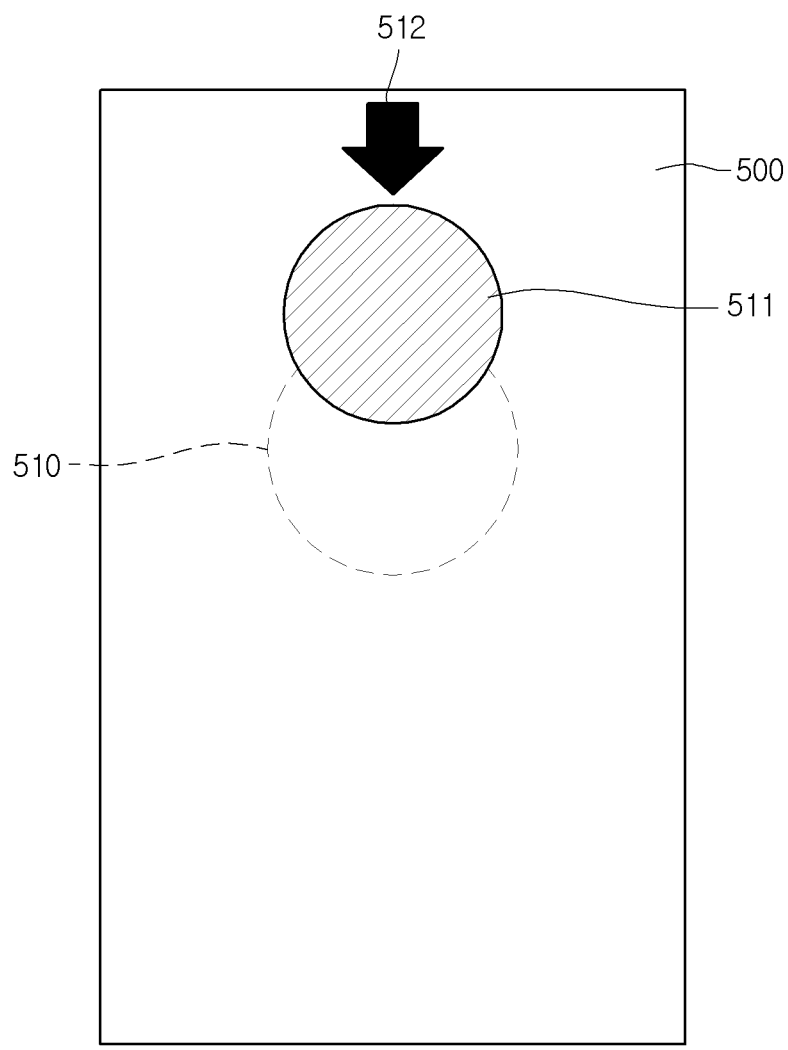

Then, as shown in FIG. 10O, when the user's finger is biased upward, as shown in FIG. 11B, a guide image 512 inducing the finger to move downward may be displayed together.

Figure 11C:
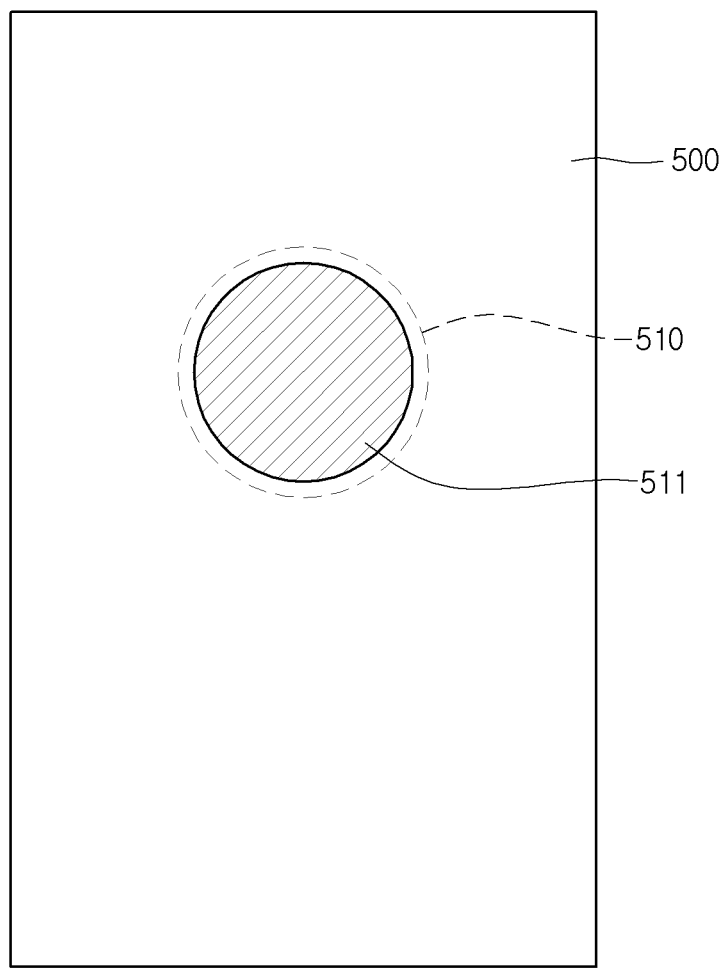

Additionally, as shown in FIG. 11C, when the user's finger is disposed at a reference position for heart rate measurement, a current position image 511 may be displayed in the reference position image 510. Then, an image, sound, or vibration notifying that a heart rate is currently measured may be generated.

Figure 11D:
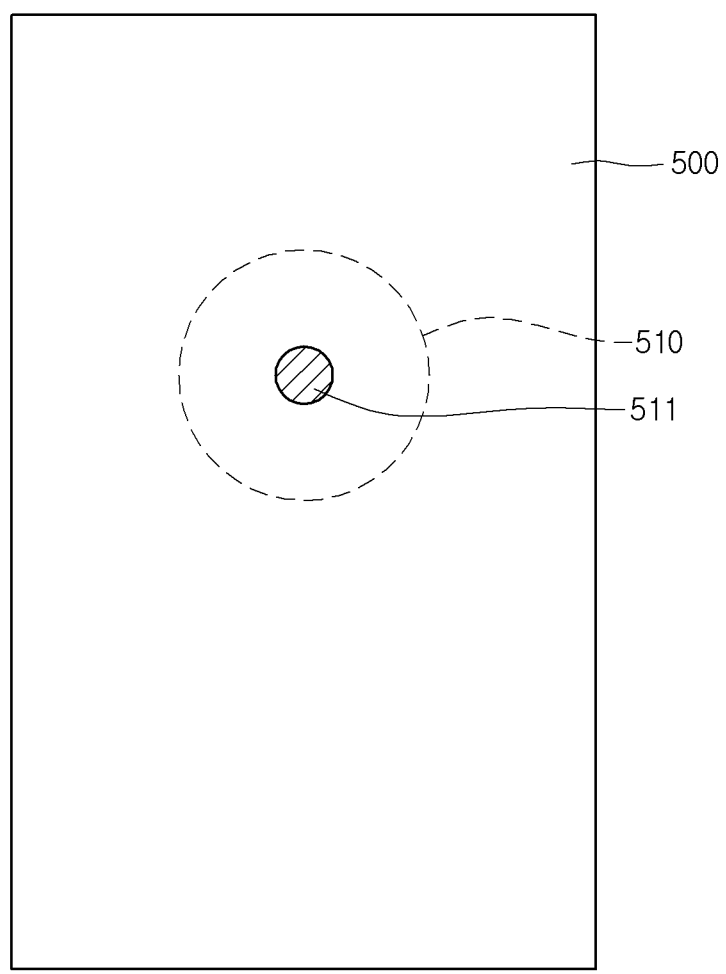

Then, when the user's finger does not contact the front glass of a back proximity sensor or the contact area of the user's finger for heart rate measurement is small, as shown in FIG. 11D, the size of the current position image 511 may be displayed small. In this case, an amount of light received by photo diodes of a light receiving device may be smaller than a reference amount and information on the finger position and information on a proper contact area of a finger may be displayed together.

Figure 12:
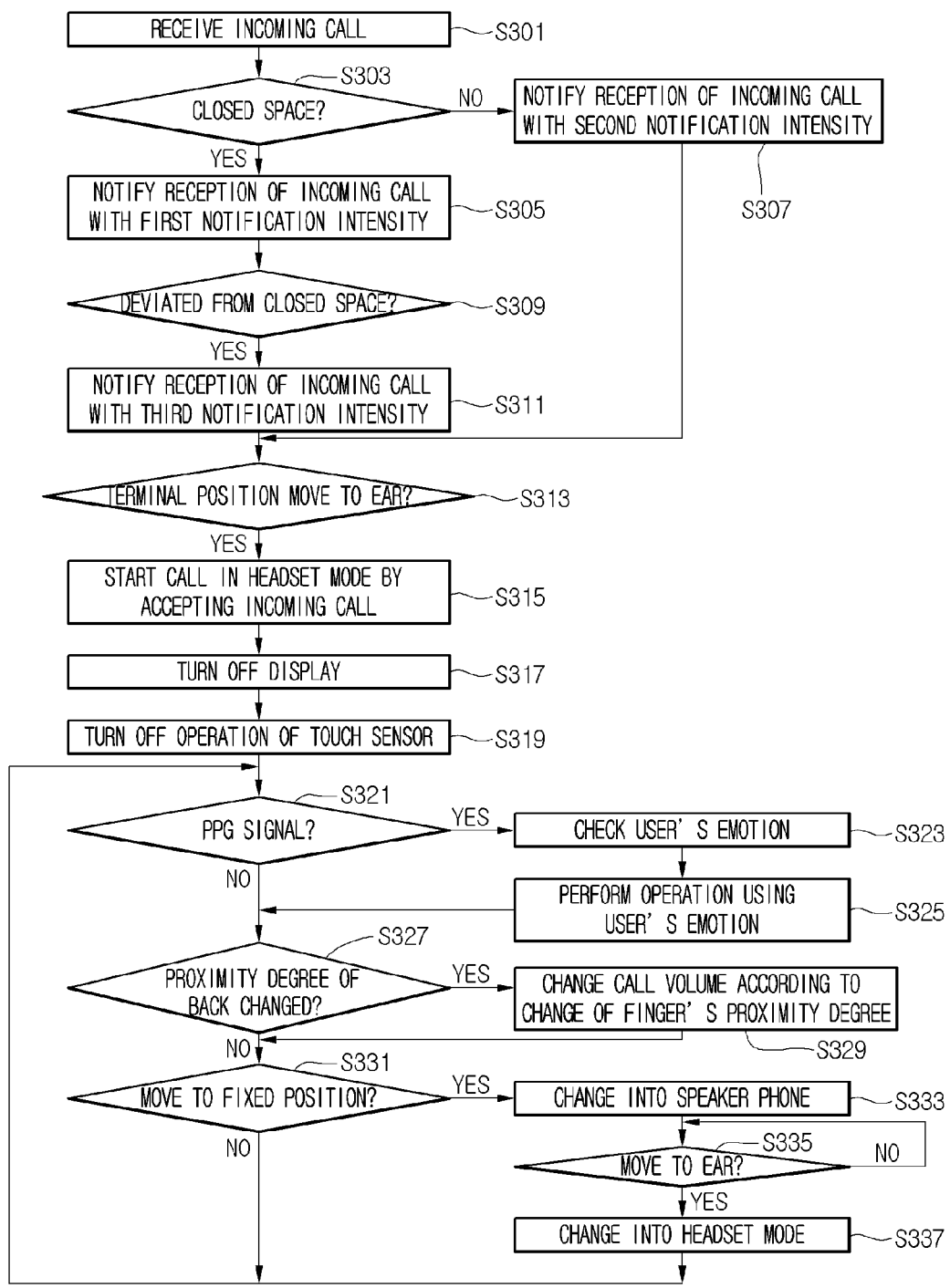
FIG. 12 is a flowchart illustrating a phone call scenario of a mobile phone according to an embodiment of the present invention.

FIG. 12 is a flowchart illustrating a phone call scenario of a mobile terminal according to an embodiment of the present invention.

When the control unit 180 receives an incoming call in operation S301, it checks whether the mobile terminal 100 is placed in a closed space in operation S303. That is, the control unit 180 checks whether the mobile terminal 100 corresponds to state information 4 or state information 7.

When the mobile terminal 100 is placed in a closed space, the control unit 180 notifies the reception of an incoming call through the output unit 150 with a first notification intensity in operation S305. The control unit 180 may notify the reception of an incoming call through at least one of sound and vibration. That is, the first notification intensity includes a first sound intensity and a first vibration intensity.

When the mobile terminal 100 is not placed in a closed space, the control unit 180 notifies the reception of an incoming call through the output unit 150 with a second notification intensity in operation S307. At this point, the second notification intensity includes a second sound intensity and a second vibration intensity. According to an embodiment of the present invention, the second notification intensity may be smaller than the first notification intensity. According to an embodiment of the present invention, the second notification intensity may be equal to the first notification intensity.

The control unit 180 checks whether the mobile terminal 100 is outside the closed space in operation S309.

When the mobile terminal 100 is outside the closed space, the control unit 180 lowers a notification intensity and then notifies the reception of an incoming call through the output unit 150 with a third notification intensity in operation S311. At this point, the third notification intensity includes a third sound intensity and a third vibration intensity. The third notification intensity may be smaller than the first notification intensity. The third notification intensity may be equal to or less than the second notification intensity. Especially, the third vibration intensity is greater than 0. Thus, when the control unit 180 performs a notification through vibration, it may set the third sound intensity to 0 and bell sound may be removed.

Then, the control unit 180 checks whether the position of the mobile terminal 100 moves to the ear in operation S313. That is, the control unit 180 checks whether the mobile terminal 100 corresponds to state information 3 or state information 5.

When the position of the mobile terminal 100 moves to the ear, the control unit 180 accepts an incoming call without a user input and initiates a call in a headset mode in operation S315, turns off the display of the display unit 151 in operation S317, and turns of an operation of a touch sensor 144 prepared at the display unit 151 in operation S319.

During a call, the control unit 180 checks whether the back proximity sensor 141b detects a PPG signal in operation S321.

When the back proximity sensor 141b detects a PPG signal, the control unit 180 checks a user's emotion of the mobile terminal 100 from the PPG signal in operation S323 and performs an operation using the checked user's emotion in operation S325.

According to an embodiment of the present invention, the control unit 180 may deliver the user's emotion to the other party's terminal during a phone call. When the control unit 180 determines that the user is overly excited from the user's emotion, it may notify an attention such as noise and sound or may terminate a phone call.

During a call, the control unit 180 may detect a change in the proximity degree of the finger through the back proximity sensor 141b in operation S327.

When a change in the proximity degree of the finger is detected through the back proximity sensor 141b, the control unit 180 changes a call volume according to the change in the proximity degree of the finger in operation S329. For example, when the finger moves away from the back proximity sensor 141b, the control unit 180 may reduce a call volume in correspondence to that the finger moves away from the back proximity sensor 141b. When the finger approaches the back proximity sensor 141b, the control unit 180 may increase a call volume in correspondence to that the finger approaches the back proximity sensor 141b. When the proximity degree of the finger does not change for a predetermined time, the control unit 180 may allow the finger to be free by fixing the call volume as the current state. Especially, the control unit 180 may fix the call volume as the current state, while outputting vibration or notification sound.

During a headset mode, the control unit 180 checks whether the position of the mobile terminal 100 moves to a fixed position such as a table or a cradle in operation S331.

When the position of the mobile terminal 100 moves to a table or a cradle, the control unit 180 changes a phone call mode from the headset mode into a speaker phone mode in operation S333. That is, when the mobile terminal 100 changes from state information 3 or state information 5 into one of state information 8 to 10, the control unit 180 changes a call mode into a speaker phone mode. In such a way, the control unit 180 may change an operation of the mobile terminal 100 by using a variety of terminal state information.

The call volume used in the speaker phone mode may be greater than that used in the headset mode. A speaker used in the speaker phone mode may be the same as or different from a speaker used in the headset mode. The speaker used in the headset mode may be positioned at the upper middle of the front of the mobile terminal 100.

In the speaker phone mode, the control unit 180 checks whether the position of the mobile terminal 100 moves to the ear in operation S335. That is, the control unit 8 checks whether one of state information 8 to 10 into state information 3 or 5.

When the position of the mobile terminal 100 moves to a table or a cradle, the control unit 180 changes a phone call mode from the speaker phone mode into the headset mode in operation S337.

Figure 13:
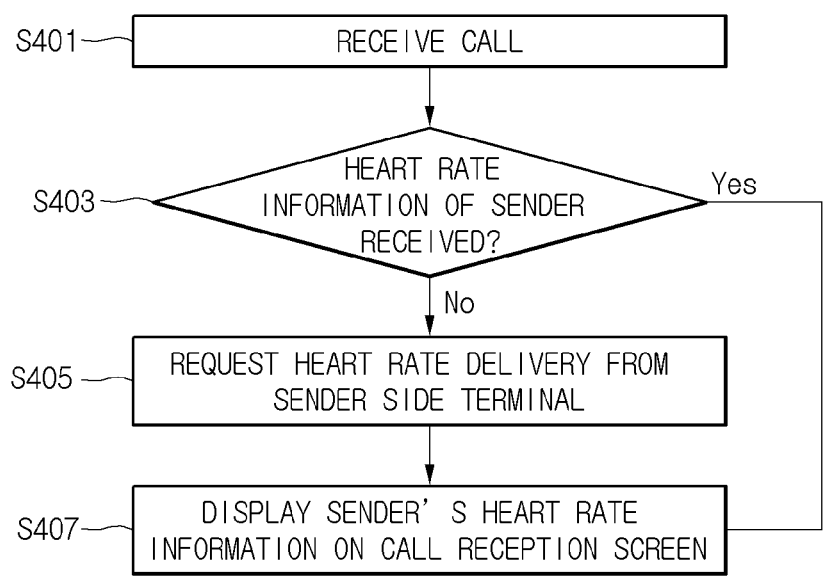
FIG. 13 is a flowchart when heart rate information is delivered or checked by using a mobile terminal according to an embodiment of the present invention.

FIG. 13 is a flowchart when heart rate information is delivered or checked by using a mobile terminal according to an embodiment of the present invention. FIGS. 14 to 20 are views illustrating UIs when heart rate information is used during call according to various embodiment of the present invention.

According to this embodiment, when the mobile terminal receives a call in operation S401, terminals are connected to each other, a first terminal receiving the call may check whether it is possible to receive the user's heart rate information of a second terminal in operation S403. That is, the user of the first terminal may check whether it is possible to check the user's heart rate state of the second terminal. Herein, the user's heart rate state of the second terminal may be a current heart rate state or a previously measured heart rate state. If a current heart rate state is delivered between users, a user of the second terminal making a phone call contacts a back proximity sensor by a finger during a phone call.

If the first terminal cannot receive heart rate information from the second terminal, the first terminal may request heart rate information transmission from the second terminal in operation S405. At this point, the second terminal may provide a UI for checking user's permission for the request and when the user of the second terminal agrees to transmit heart rate information together, the second terminal transmits the user's current heart rate information to the first terminal.

Then, information such as a phone number or a photo of the other party who makes a phone call may be displayed and also the user's heart rate information of the second terminal may be displayed through various methods such as a text, an image, sound, or vibration.

Various embodiments relating thereto are described with reference to FIGS. 14 to 20.

Figure 14:
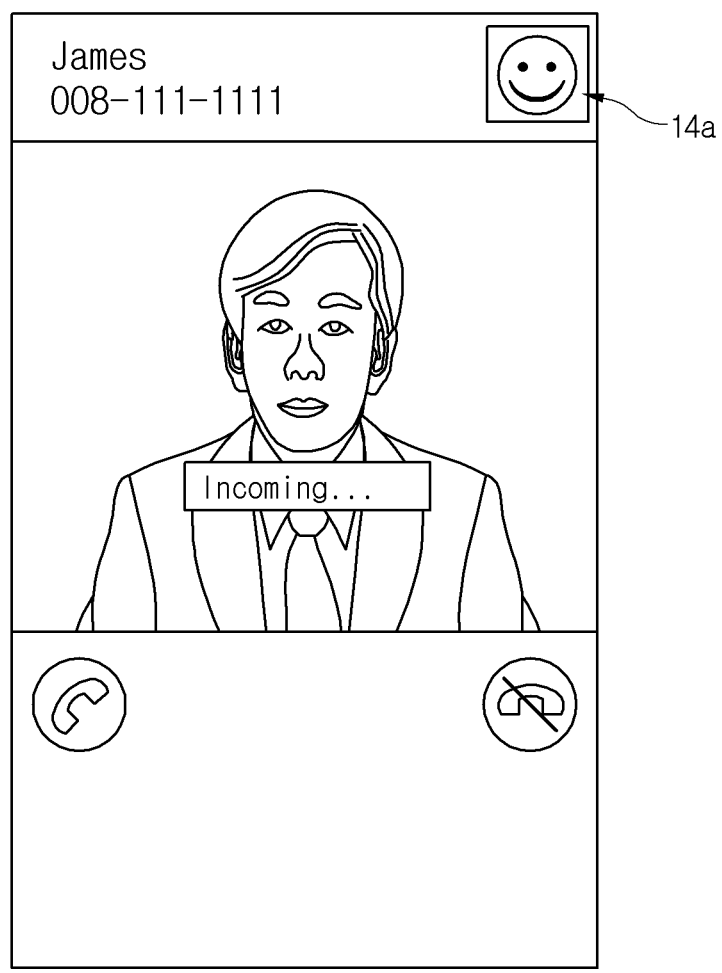
FIGS. 14 to 20 are views illustrating UIs using heart rate information during a call according to various embodiments of the present invention.

First, referring to FIG. 14, the screen of the first terminal receiving a call displays information on the second terminal making a call, for example, a name, a phone number, or a predetermined user photo of the second terminal. Then, the user's heart rate information of the second terminal delivered from the second terminal may be displayed as a user state icon 14a.

That is, a UI shown in FIG. 14, as the screen of the first terminal receiving a call signal, may display information on the second terminal requesting a call signal or the second terminal user, and also displays the user state icon 14a representing the user's heart rate information of the second terminal on the screen. The user state icon 14a may be displayed as an icon including a yellow image or a smiling image when the heart rate of the second terminal user is within a predetermined normal range in order to allow the first terminal user to check the other party's state easily. On the contrary, when the heart rate of the second terminal user is not within a predetermined normal range, the user state icon 14a may be displayed with dark color or an icon including a wry face in order to allow the first terminal user to check the other party's state easily.

Figure 15:
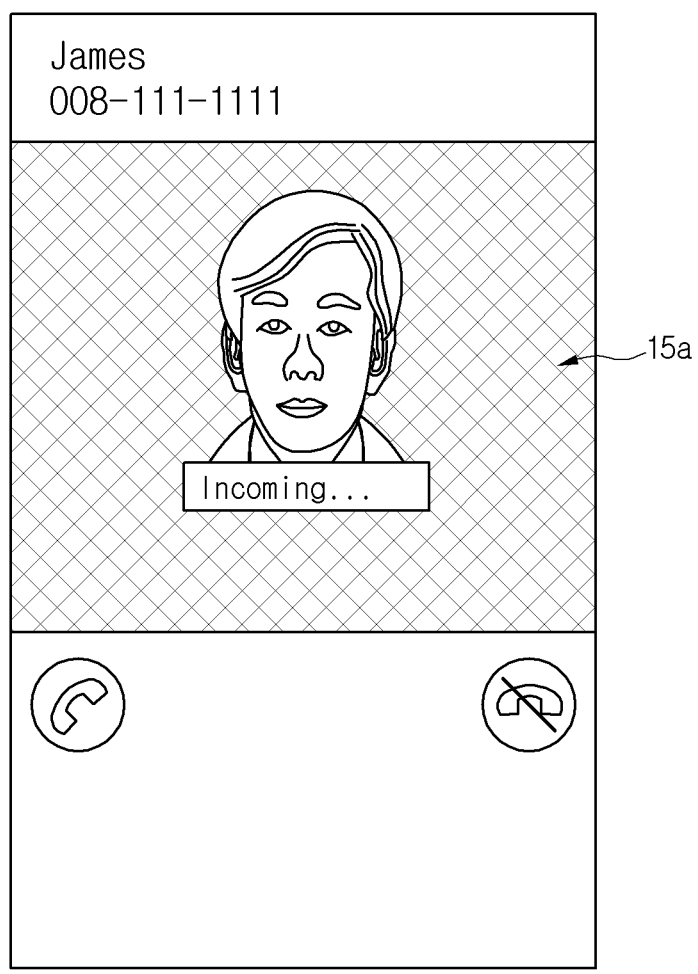

Then, as shown in FIG. 15, instead of displaying the heart rate information of the second terminal user as an icon, it is possible to change the color of a photo of the second terminal user pre-stored in the first terminal.

That is, when a contact photo representing the second terminal or the second terminal user is pre-stored in the first terminal, the control unit of the first terminal may change the background color 15a of the contact photo according to the heart rate information received from the second terminal. For example, the when the received heart rate information of the second terminal user is within a normal range, a corresponding contact photo may be displayed on the background screen having yellow or green color with a warm feeling. Then, when the received heart rate information of the second terminal user is not within the normal range, the background color (15a) may be displayed with stimulating colors such as red.

The first terminal may display an icon as information on the second terminal making a call together or may edit a contact photo according to the heart rate information delivered from the second terminal.

Figure 16:
Figure 17:
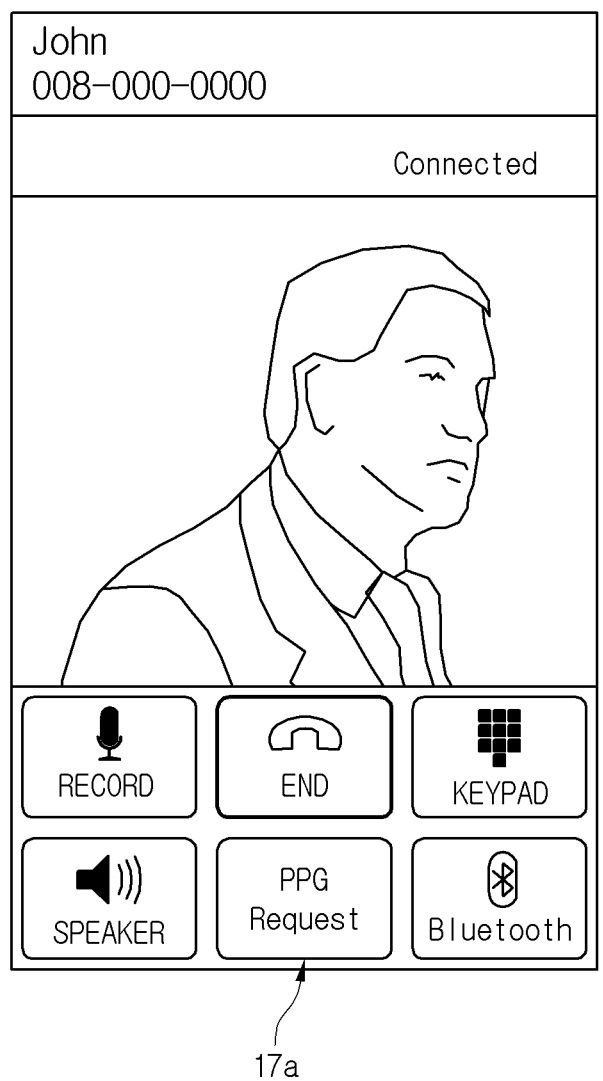

Additionally, as shown in FIG. 16, the first terminal may change a pre-stored contact photo to another photo according to the heart rate information from the second terminal. For example, when the heart rate of the second terminal user is high abnormally, instead of displaying a pre-stored contact photo on a call reception screen, a stimulating photo representing a psychological state of the second terminal user may be displayed. Likewise, instead of a contact photo representing the second terminal or the second terminal user, it is possible to display a photo representing a calm feeling.

FIGS. 17 to 20 are views of UIs illustrating processes for sharing heart rate information between a first terminal and a second terminal.

As descried above, when the heart rate information of the second terminal user is not delivered together, a user of the terminal receiving a call may transmit a message requesting the delivery of the heart rate information to the second terminal.

At this point, the first terminal user may check a name, a phone number, or a contact photo, as information on the second terminal displayed during call reception and may check an icon or an image representing the heart rate information. Then, when the heart rate information of the second terminal user is not displayed, the first terminal user may select a menu 17a (that is, PPG Request) for requesting heart rate information transmission.

Figure 18A:
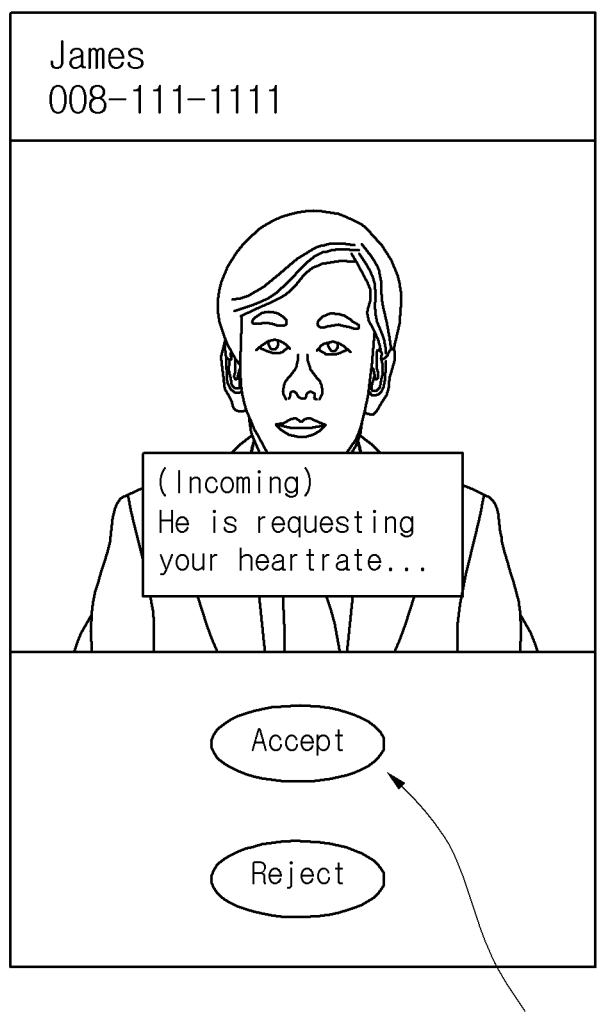

When the heart rate information transmission request is delivered from the first terminal to the second terminal, as shown in FIG. 18A, a message that a request for the heart rate information transmission arrives from the first terminal attempting to make a call or connected for a call and also an Accept/Reject menu 18a for selecting whether to accept or reject the request may be displayed on the second terminal.

Figure 18B:
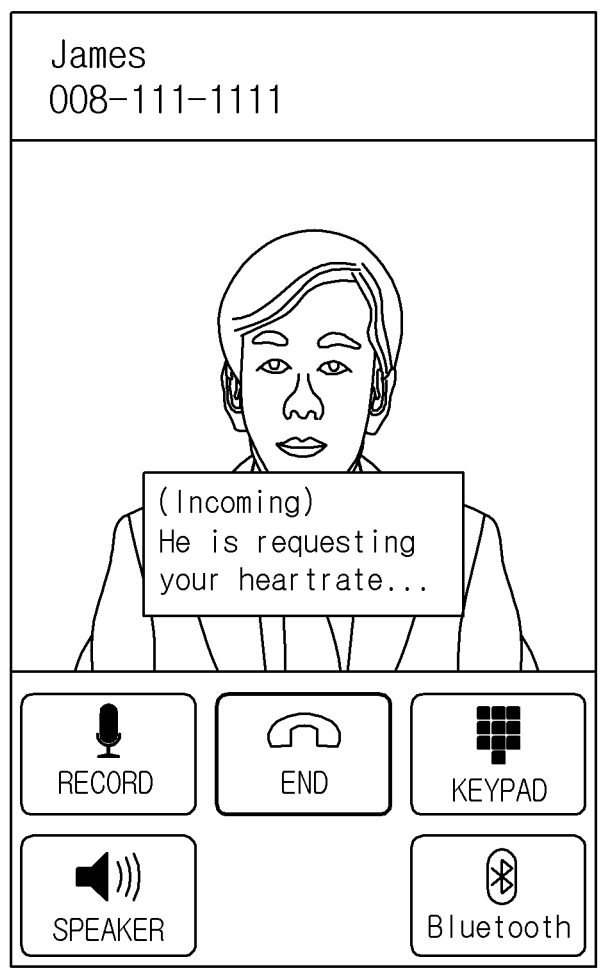

Then, when the second terminal user selects one of the Accept/Reject menu 18a, as shown in FIG. 18B, a UI for typical call connection may be displayed.

Figure 18C:
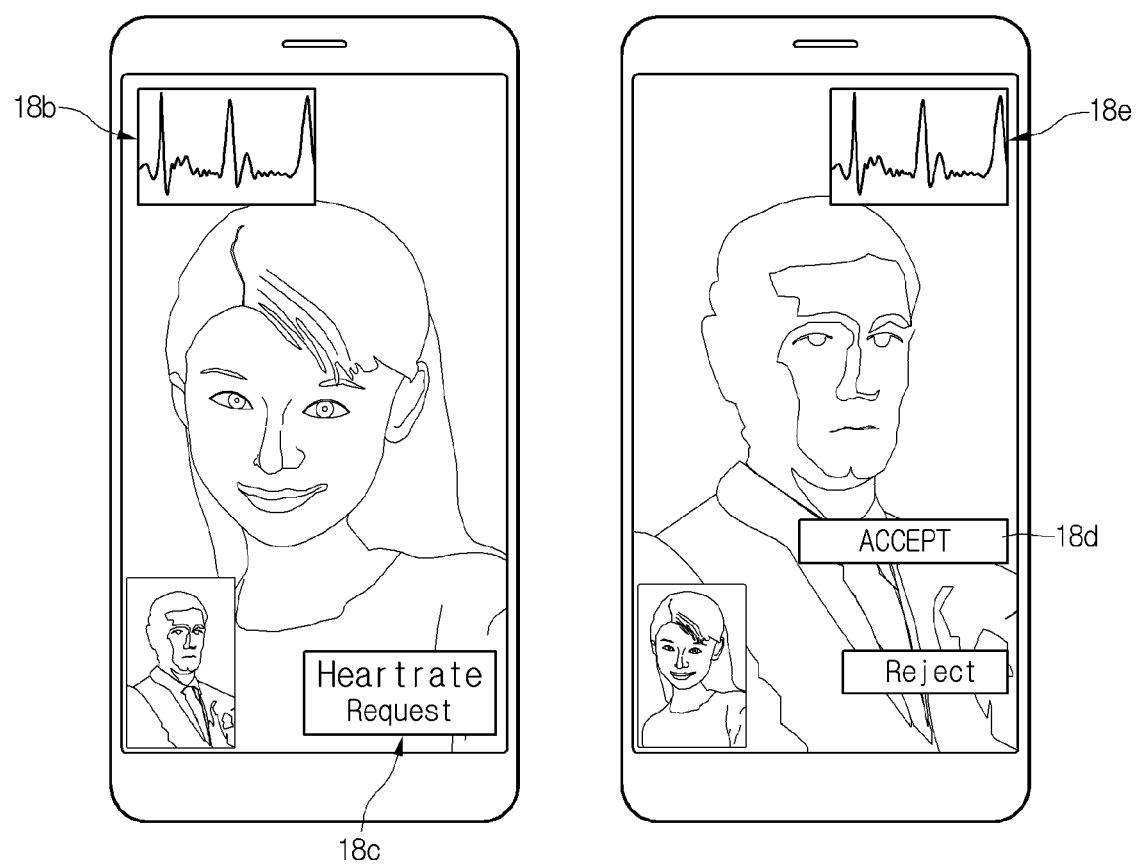

Additionally, when a video call is made between users, heart rate information may be requested or a requested item may be accepted. As shown in FIG. 18C, when a video call is connected between the first terminal user and the second terminal user, a message for requesting heart rate information transmission may be delivered from the first terminal to the second terminal. That is, the menu 18c for requesting heart rate information may be displayed on the screen.

Then, when the second terminal user makes a video call and selects a menu 18d for accepting the heart rate information transmission displayed on a screen, the heart rate information of the second terminal user may be transmitted to the first terminal. The heart rate information transmitted at this point may be pre-stored heat rate information or current heart rate information measured during the video call.

Then, the heart rate information of the second terminal user may be displayed as a heart rate graph image 18b on the screen of the first terminal, that is, the screen during the video call and when the heat rate information is shared between users, the heart rate information of the first terminal user may be displayed as a heart rate graph image 18e on the screen of the second terminal, that is, the screen during the video call. Through such an embodiment, the heart rate information on one side or both sides may be displayed on a screen, and this may be applied to medical fields.

Figure 18D:
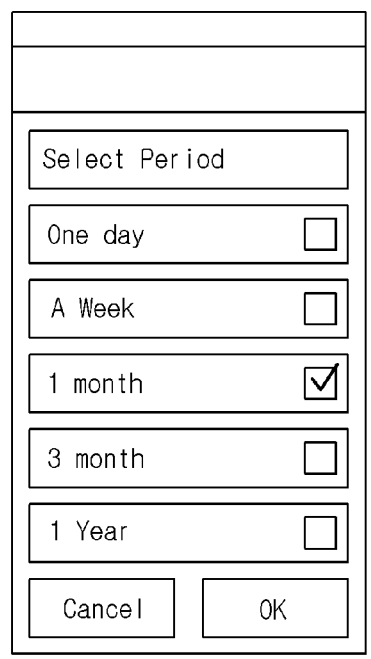

Then, besides the Accept/Reject menu, it is possible to set a period and deliver one of pre-stored heart rate information in the second terminal receiving a message for requesting heart rate information transmission from the first terminal and as shown in FIG. 18D, the second terminal user may set a period and transmit one of pre-stored heart rate information.

Then, when the second terminal user requests a call from the first terminal and the first terminal user receives an incoming call, a PPG signal delivery may be instructed or a call connection is made with a PPG signal request.

Figure 19:
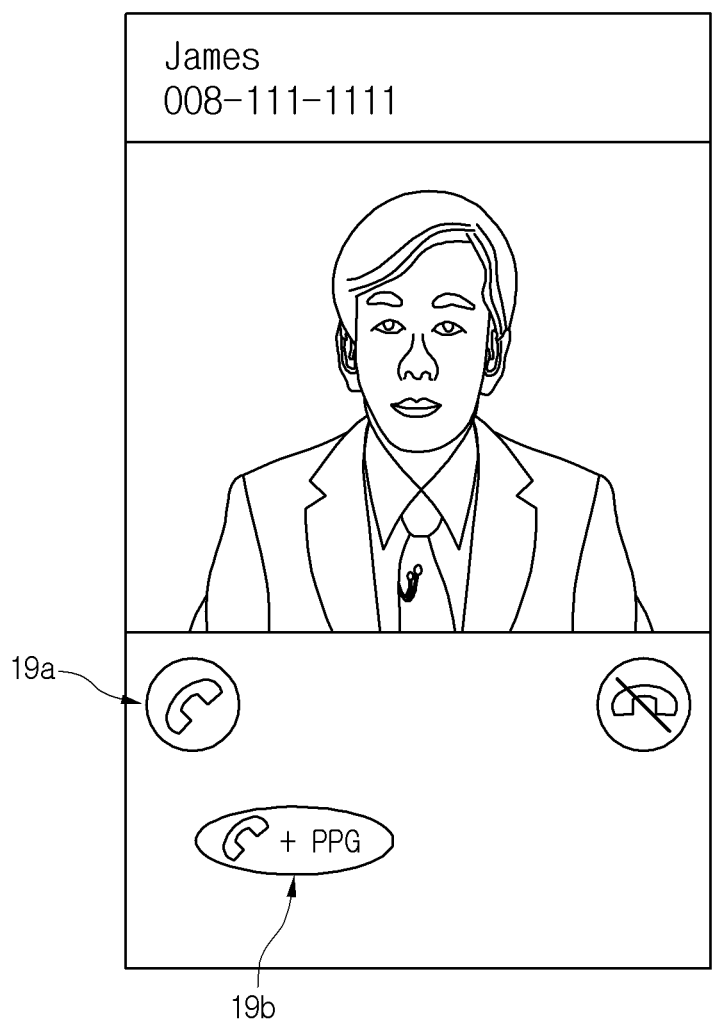

As shown in FIG. 19, when the second terminal requests a call signal from the first terminal, that is, the second terminal user makes a call to the first terminal, a first call button 19*a* for a call connection without delivering heart rate information and a second call button 19*b* for a call connection with delivering heart rate information may be displayed together.

In this case, the second terminal user may select whether to transmit a PPG signal together from a request stage of a call signal.

The first terminal user may check the heart rate information of the second terminal user together when there is an incoming call and may consider a psychological state of the other party during a phone call.

Figure 20:
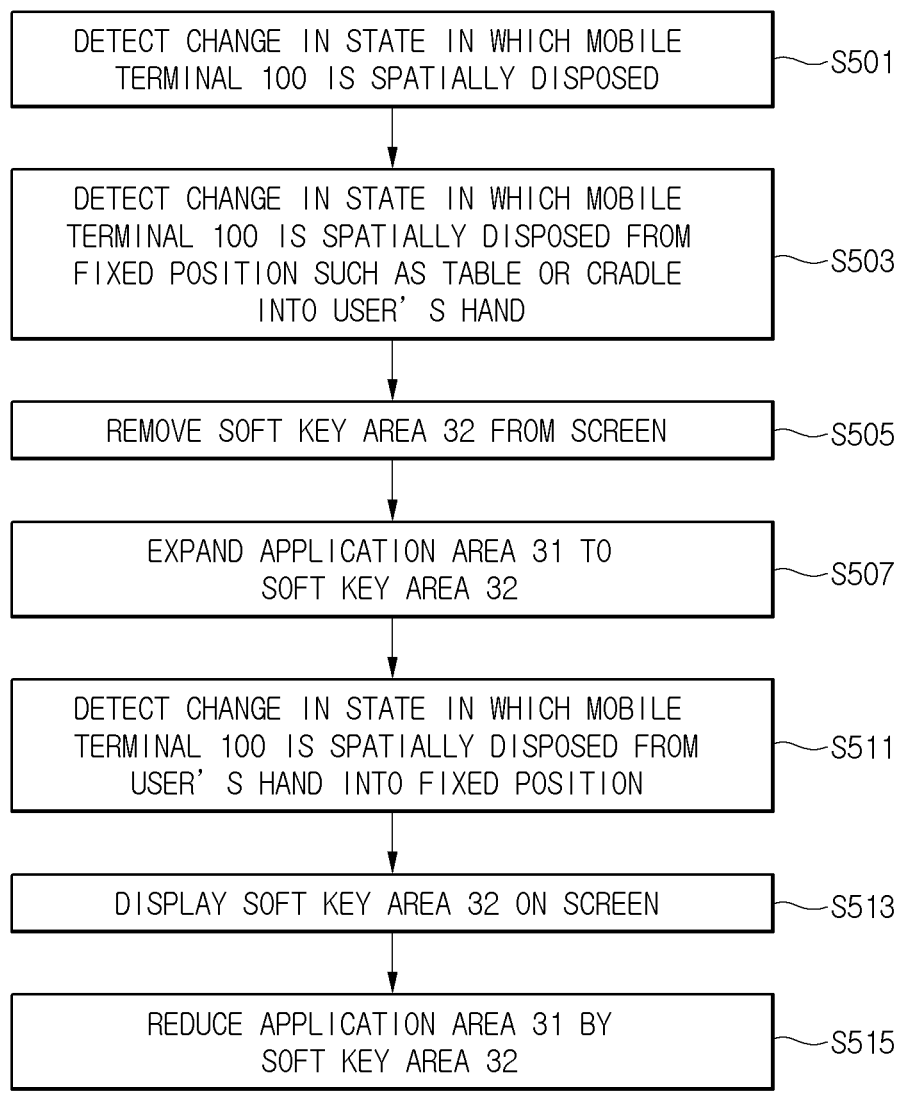

FIG. 20 is a flowchart illustrating a soft key control scenario of a mobile terminal according to an embodiment of the present invention.

The control unit 180 detects a change in state in which the mobile terminal 100 is spatially placed in operation S501.

When the state in which the mobile terminal 100 is spatially placed changes from the fixed position such as a table or a cradle into the user's hand in operation S503, the control unit 180 removes a soft key area 32 from a screen in operation S505 and expands an application area 31 to the soft key area 32 in operation S507. That is, it is checked whether any one state of state information 8 to 10 on the terminal changes into state information 1 or state information 3, state information 5 or state information 6 and accordingly, the display of a soft key corresponding to a user input unit for controlling an operation of the terminal and displayed on a screen may be determined.

Even when the soft key disappears, a user may perform the role of the soft key through at least one back key 131. Therefore, a user may execute an application by using a broad screen.

When the state in which the mobile terminal 100 is spatially placed changes from the user's hand into the fixed position in operation S511, the control unit 180 displays the soft key area 32 and reduces the application area 31 in correspondence to the soft key area 32 in operation S515. This is because a user may have a difficulty in manipulating the back key 131 if the mobile terminal 100 is disposed at the fixed position.

Figure 21A:
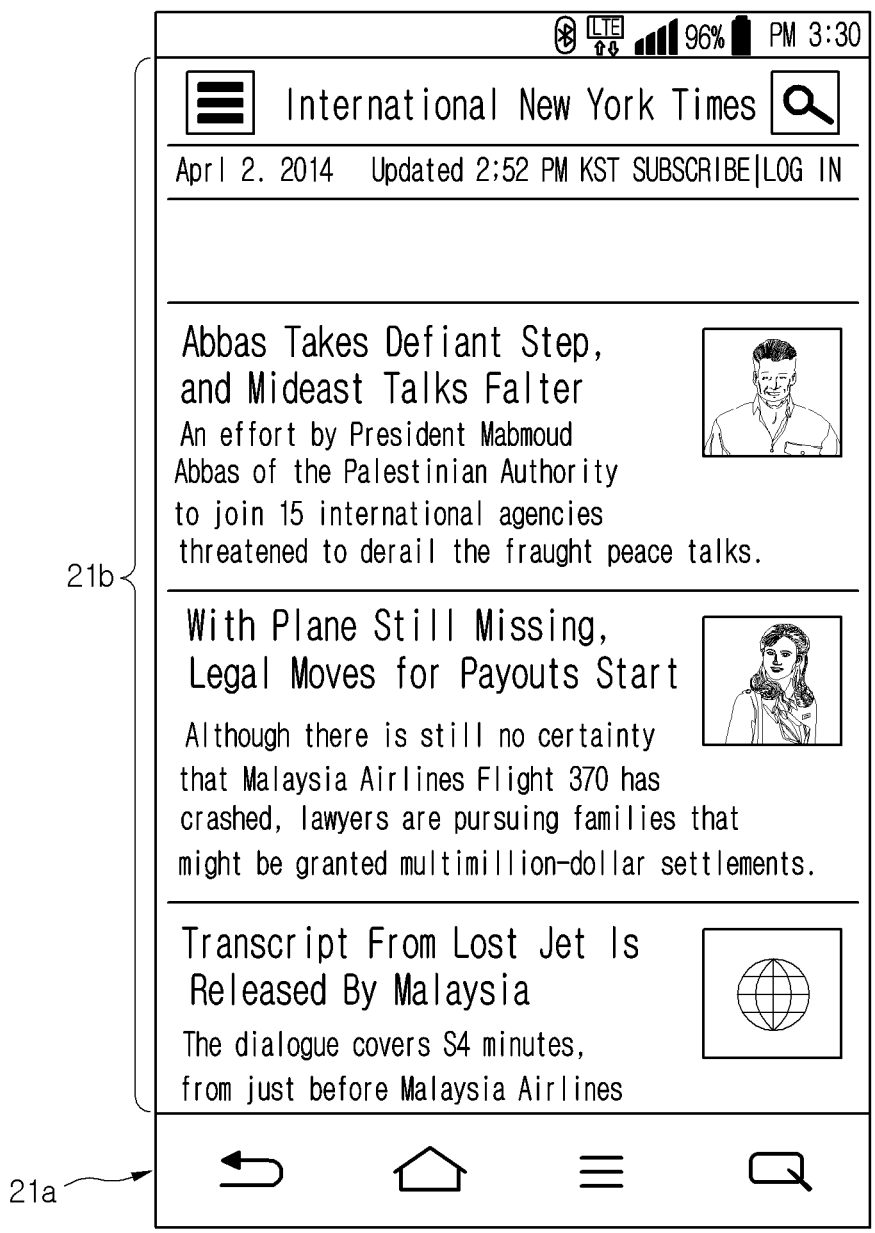
FIGS. 21A and 21B are views when a soft key is displayed or not displayed on the basis of state information on a terminal according to an embodiment of the present invention.
Figure 21B:
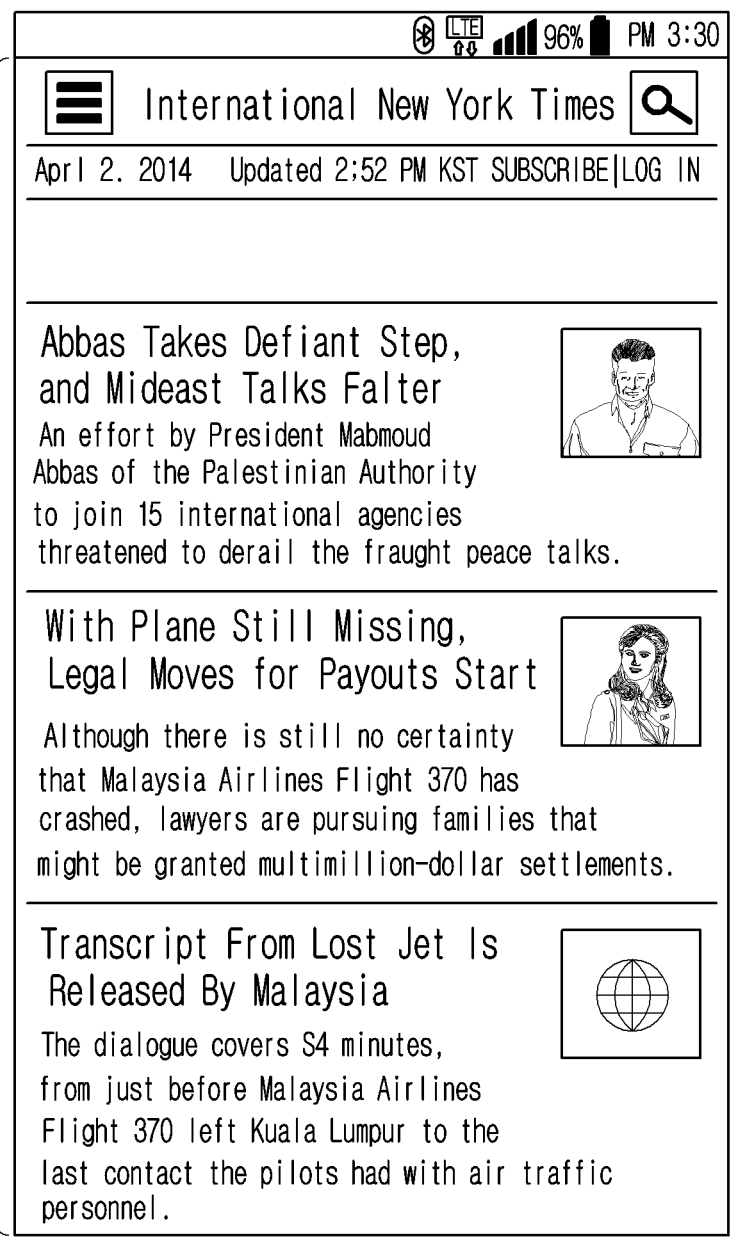
Figure 22A:
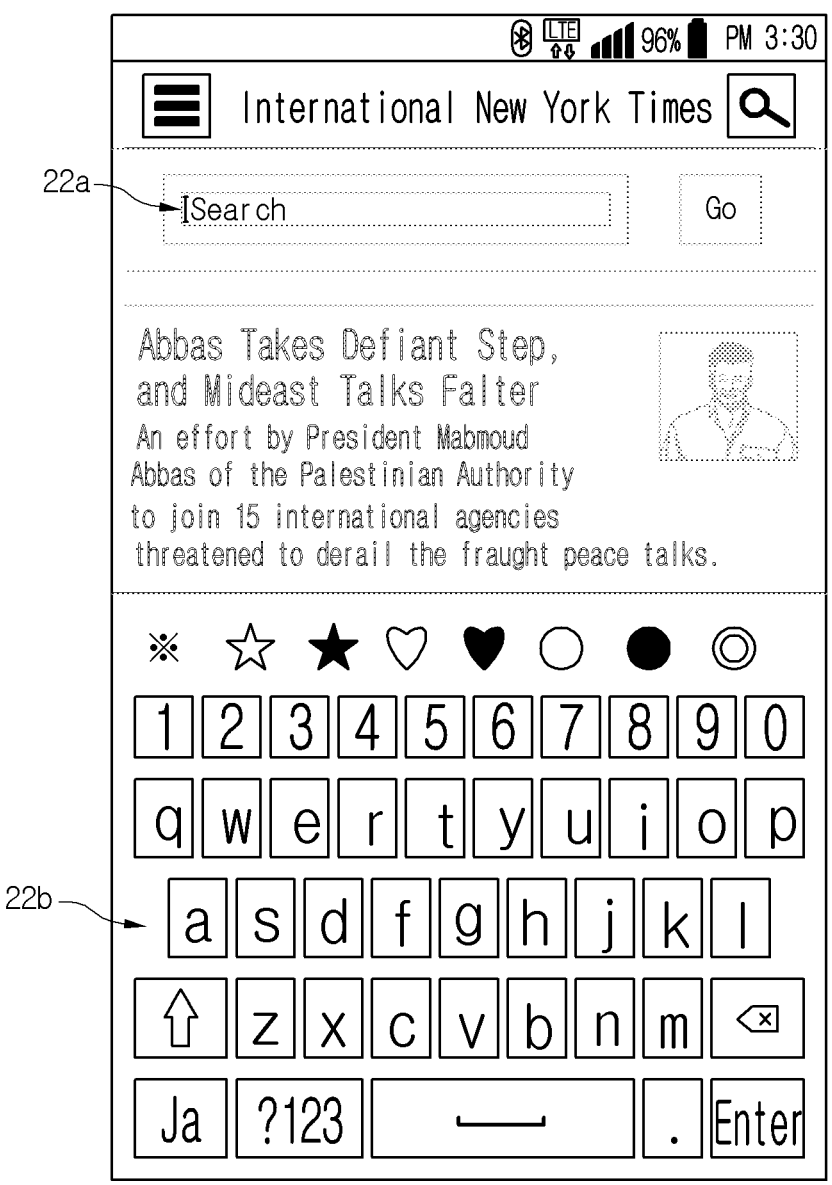
FIGS. 22A and 22B are views when a keypad is displayed or not displayed on the basis of state information on a terminal according to an embodiment of the present invention.
Figure 22B:

FIGS. 21A and 21B are views when a soft key is displayed or not displayed on the basis of state information of a terminal according to an embodiment of the present invention. FIGS. 22A and 22B are views when a key pad is displayed or not displayed on the basis of state information of a terminal according to an embodiment of the present invention.

First, referring to FIGS. 21A and 21B, a terminal may determine whether to display a soft key displayed on a screen according to checked terminal state information. In the case of state information 1, state information 3, state information 5, and state information 6, that is, when a user grabs a terminal, the control unit 180 displays a soft key 21*a* as a user input unit for smooth input of a user in a designated area.

Then, when one of terminal state information 1, 3, 5, or 6 changes into one of terminal state information 8, 9, or 10, the control unit 180 controls a soft key not to be displayed so that the size of an information area 21*b* other than that is displayed larger.

That is, when a user places a terminal at a fixed position while grabbing the terminal, through the back proximity sensor, the control unit 180 of the terminal determines that the user watches a screen displayed on the terminal instead of manipulating the terminal and expands the information area 21*b* to an area where a soft key is displayed.

In such a way, the control unit 180 may control an operation of the terminal on the basis of the detected state information of the terminal and additionally, may control an operation of the terminal to be changed according to the terminal state information. For example, when the color of an object detected through the back proximity sensor changes into a color other than the color of a hand, the control unit 180 may determine this as a user's intention for extending the information area 21*b*.

Then, referring to FIGS. 22A and 22B, the control unit 180 of the terminal may display a keypad on a screen or perform a hide operation automatically when the terminal state information changes. For example, when a state of the terminal changes from one of state information 8, 9, and 10 into one of state information 1, 3, 5, and 6, the control unit 180 may display the key pad 22*b* in a corresponding screen. In this case, when a terminal is placed at a table or a cradle and a user moves it by the hand, the control unit 180 may determine this as a gesture for inputting a command such as a text.

Then, characters inputted by the key pad 22*b* may form a cursor at a text input available position in a corresponding screen. For example, when an internet site is displayed on a screen, the control unit 180 may automatically select a text input available item in a corresponding web page.

On the contrary, when a state in which a user grabs a terminal (that is, one of state information 1, 3, 5, and 6) into a state in which the position of the terminal is fixed at an object such as a table or a cradle (that is, one of state information 8, 9, and 10), a generated key pad UI 22*b* may not be displayed.

Then, a pedestrian mode control scenario of the mobile terminal 100 according to an embodiment of the present invention is described with reference to FIG. 23.

Figure 23:
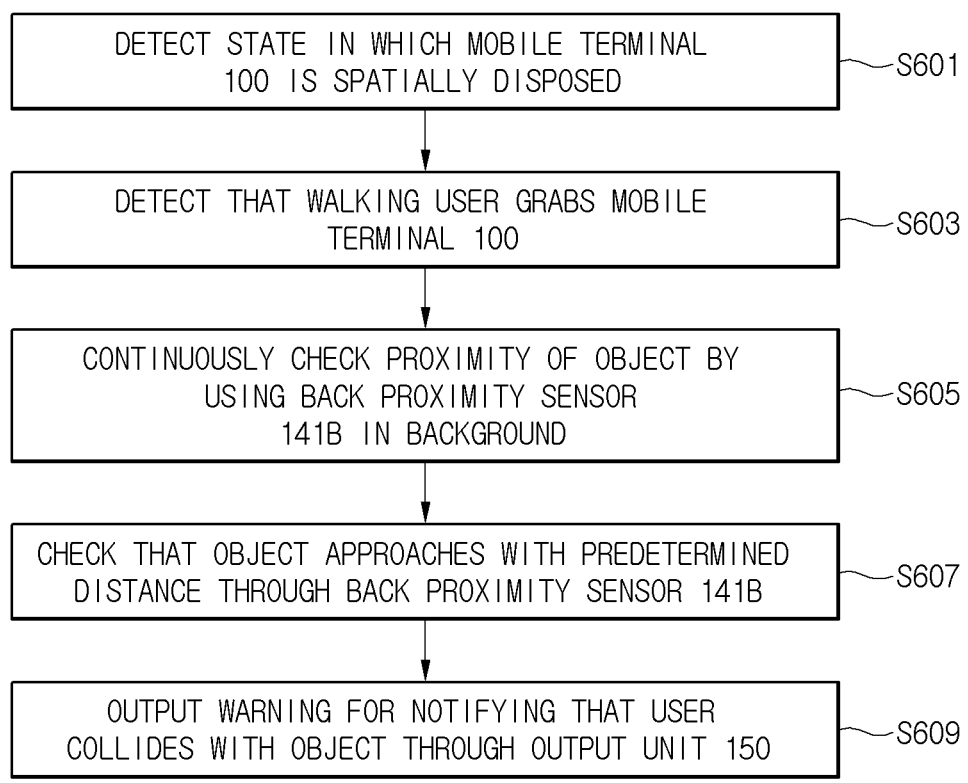
FIG. 23 is a flowchart illustrating a walking assist scenario of a mobile terminal according to an embodiment of the present invention.

FIG. 23 is a flowchart illustrating a walking assist scenario of a mobile terminal according to an embodiment of the present invention.

The control unit 180 may notify a user's danger situation on the basis of various state information of a terminal.

First, the control unit 180 detects a state in which the mobile terminal 100 is spatially placed in operation S601. That is, the state information of the terminal is determined by using at least one sensor of the sensing unit 140.

Then, when the control unit 180 determines that a walking user grabs the mobile terminal 100 by the hand in operation S603, even when an application is executed in a foreground, the control unit 180 continuously checks the proximity of an object by using the back proximity sensor 141*b* in operation S605.

Here, when the control unit 180 determines that a walking user grabs the mobile terminal 100 by the hand, this may corresponds to the above-mentioned state information 11 or state information 12 of a terminal. Besides that, in the case of one of state information 1, state information 5, and state information 6 of a terminal, even when a specific application is being executed in the terminal, the control unit 180 may continuously check the proximity of an object by the back proximity sensor 141*b*.

Then, when the control unit 180 checks that an object approaches within a predetermined distance through the back proximity sensor 141*b* in operation S607, the control unit 180 may output a warning notifying that a user is going to collide with an object through the output unit 150 in operation S609.

By using the back proximity sensor 141*b* operating on the background, various UIs provided from an application in execution are described.

Figure 24:
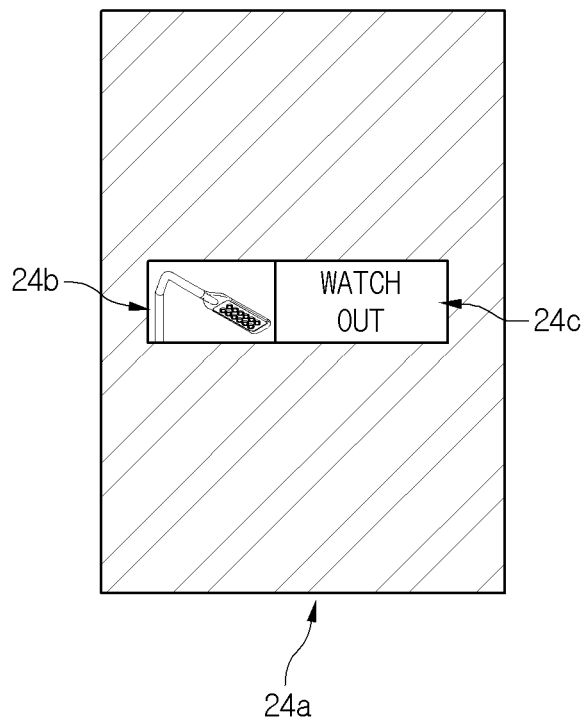
FIG. 24 is a view illustrating a warning UI by a back proximity sensor according to an embodiment of the present invention.

FIG. 24 is a view illustrating a warning UI by a back proximity sensor according to an embodiment of the present invention.

Referring to FIG. 24, in the case that a user grabs a terminal by the hand and moves, when the proximity of an object is detected by the back proximity sensor 141b, the control unit 180 may display a warning background image 24a, a warning message 24c, or a warning icon 24b on a screen.

At least one of the warning background image 24a, the warning message 24c, or the warning icon 24b may be displayed on a screen of the display unit 151 and displays of such images and notification by sound or vibrations are possible.

When a user walks while watching a video, a UI provided when the proximity of an object is detected by the back proximity sensor 141b is described.

Figure 25A:
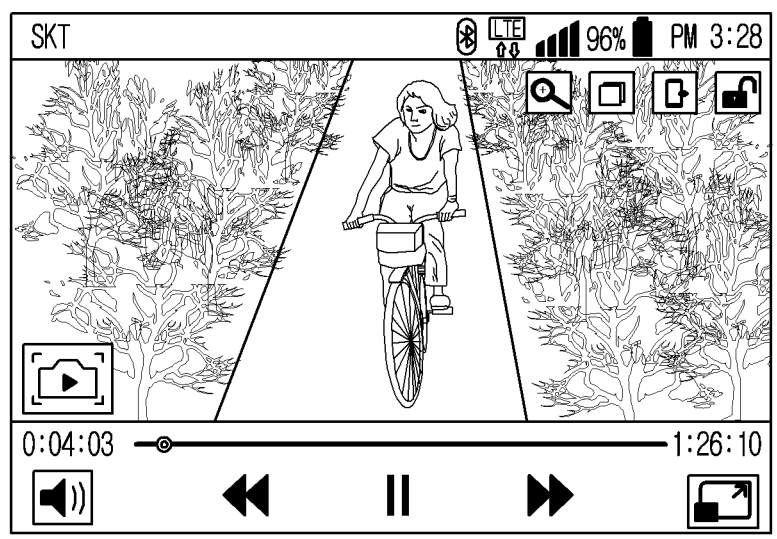
FIGS. 25A and 25B are views when a warning is notified to a user during watching a video according to an embodiment of the present invention.
Figure 25B:
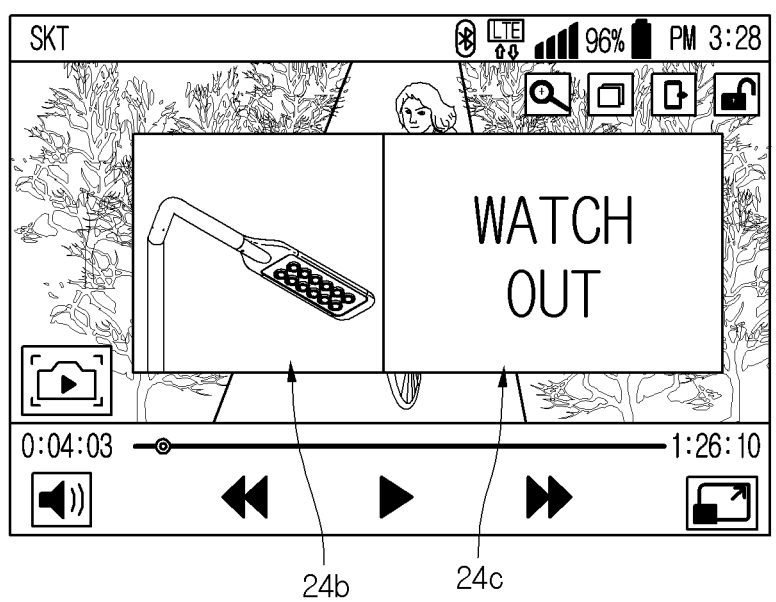

FIGS. 25A and 25B are views when a warning is notified to a user during watching a video according to an embodiment of the present invention.

When it is determined that a user is walking, that is, a movement of a terminal is detected by the acceleration sensor 142, the control unit 180 operates the back proximity sensor 141b as a background and checks the proximity of an object at the back periodically or continuously.

Then, while a user watches a video, when the proximity of an object is detected by the back proximity sensor 141b, the control unit 180 may stop the playback of the video that the user watches and as shown in FIG. 25B, may output the warning icon 24b or the warming message 24c.

Then, when the proximity of an object is checked by the back proximity sensor 141b, the control unit 180 may display an image (an image or a video) captured by a back camera on an entire or portion of a displayed video area. That is, the control unit 180 may allow a user to directly check a dangerous situation captured by a back camera.

Figure 26A:
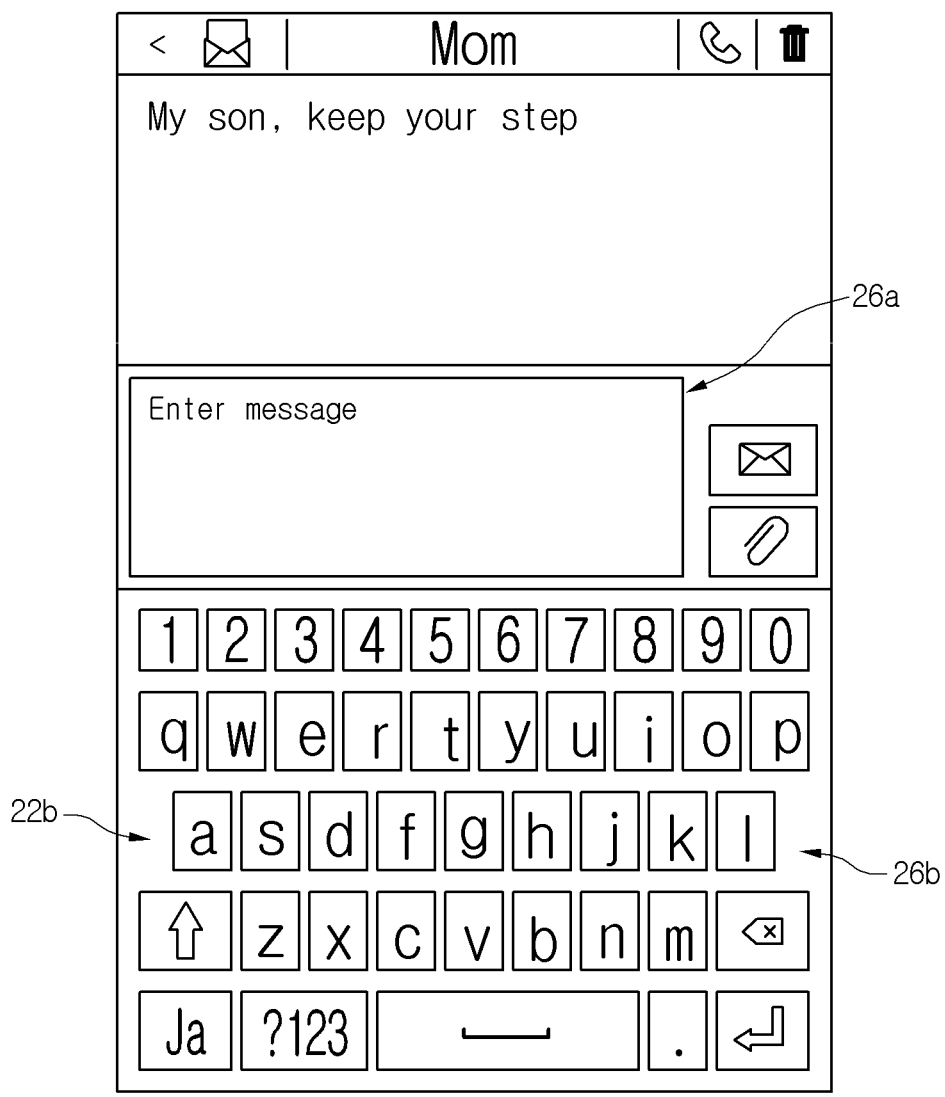
FIGS. 26A to 26C are views when a warning is notified to a user in a message application according to an embodiment of the present invention.
Figure 26B:
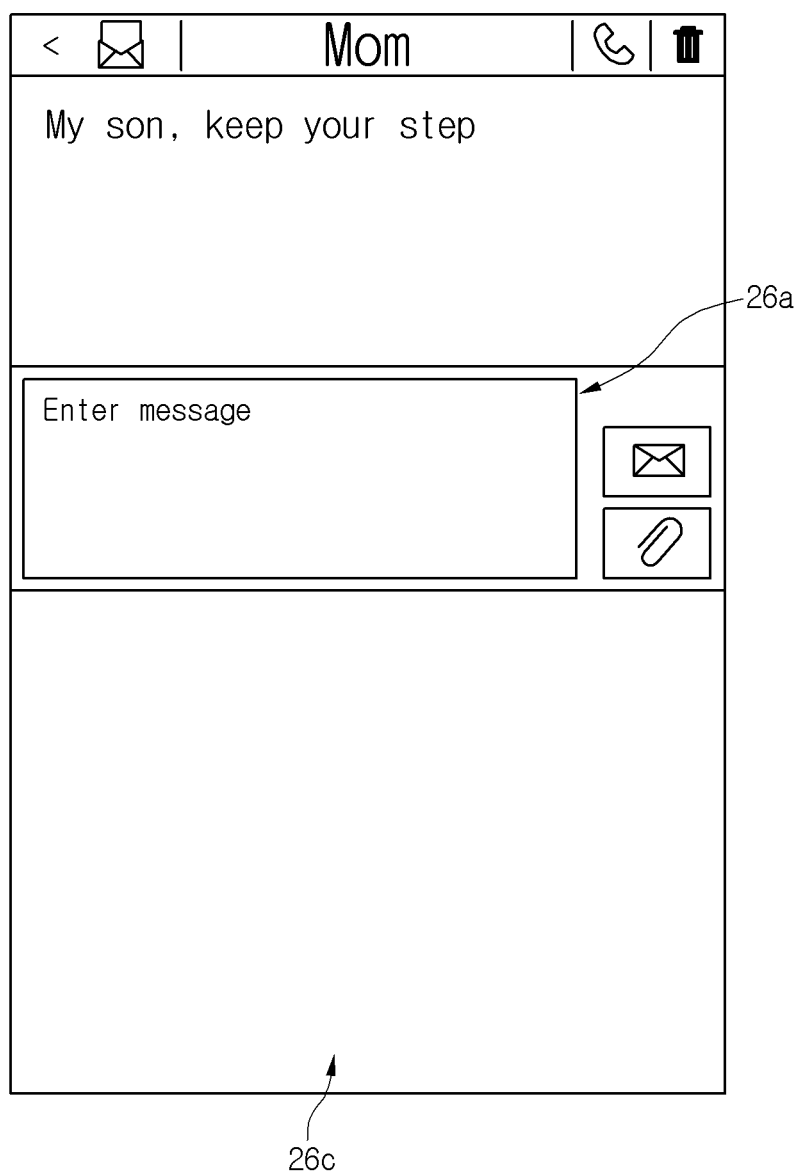
Figure 26C:
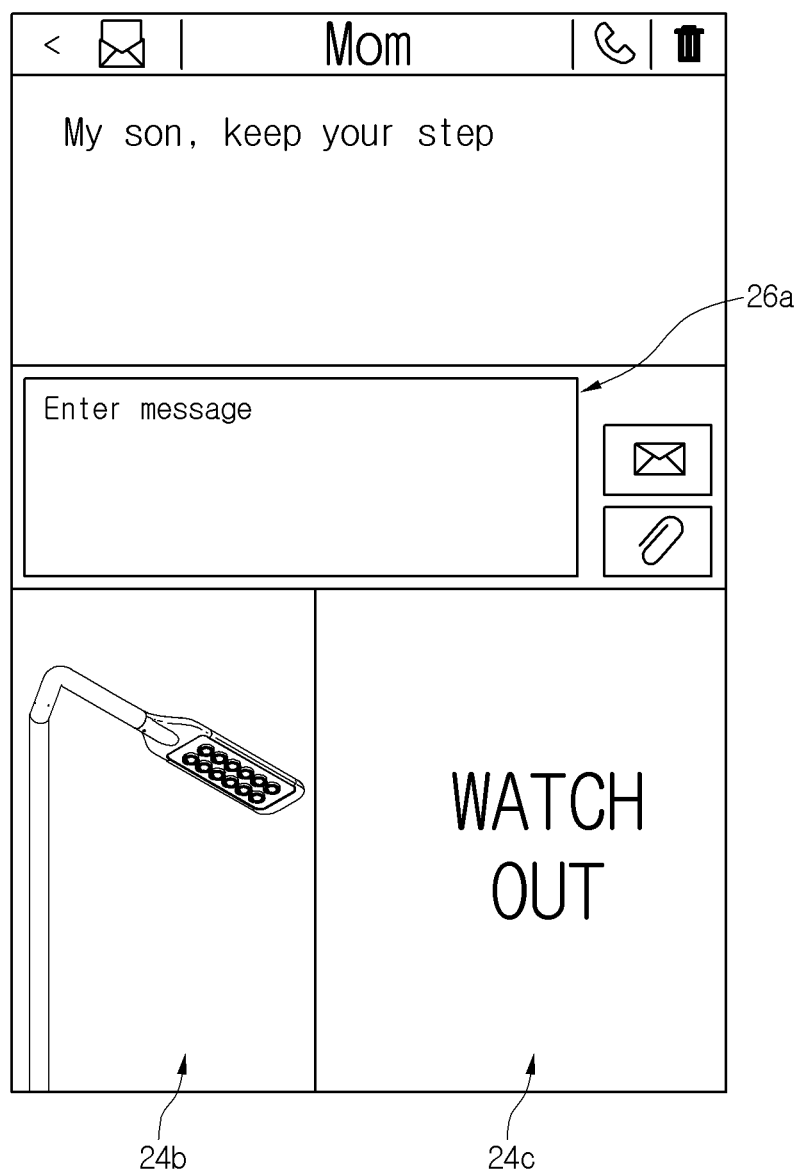

FIGS. 26A to 26C are views when a warning is notified to a user in a message application according to an embodiment of the present invention.

Whiles a user executes an application for inputting a text like a message application and walks, a virtual key pad 26b and a text input window 26a are displayed on a screen of a terminal.

Then, when the proximity of an object is detected by the back proximity sensor 141b, as shown in FIG. 26B, the control unit 26 may display a block image 26c for preventing a user from inputting a text through a displayed circuit keypad 26b.

Additionally, when the proximity of an object is detected by the back proximity sensor 141b, in order to prevent a user from paying attention to a virtual key pad, a warning icon 24b or a warning message 24c may be displayed on entire or part of a screen on the virtual key pad.

Through such an operation, a user may be prevented from inputting a message. Then, instead of stopping an operation of the displayed virtual key pad, an image or a message that notifies a danger may be outputted to entire or part of a screen of the display unit.

In addition to a message application, like an internet application, such an embodiment may be applicable to various applications in which a user inputs a text by using a virtual key pad.

Figure 27A:
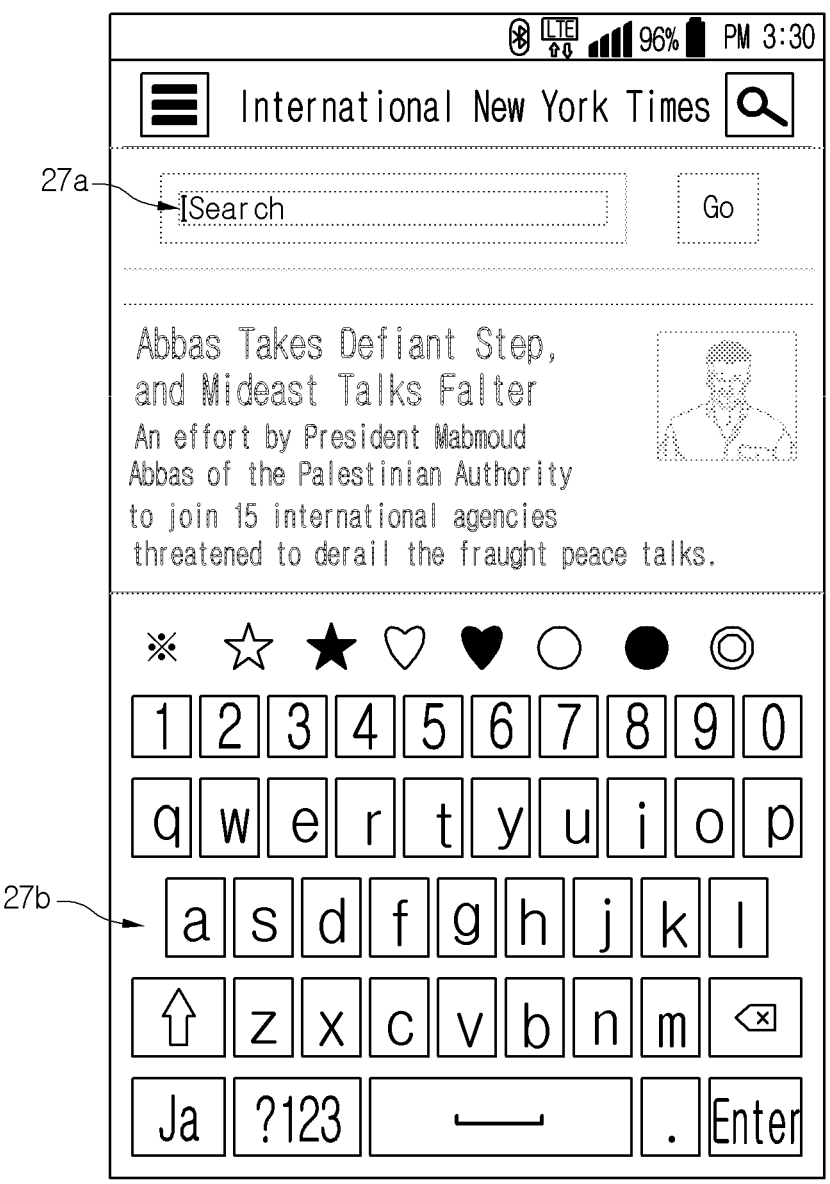
FIGS. 27A to 27C are views when a warning is notified to a user in an internet application according to an embodiment of the present invention.
Figure 27B:
Figure 27C:

FIGS. 27A to 27C are views when a warning is notified to a user in an Internet application according to an embodiment of the present invention.

As shown in FIG. 27A, when the virtual key pad 27b is displayed and a user manipulates the virtual key pad 27b to input a search word in a search window 27a, as shown in FIG. 27B, a block image 27c covering the virtual key pad 27a may be displayed. Then, as shown in FIG. 27C, the warning icon 24b or the warning message 24c may be outputted.

Then, an automatic focus adjustment scenario of the mobile terminal 100 according to an embodiment of the present invention will be described with reference to FIG. 28.

Figure 28:
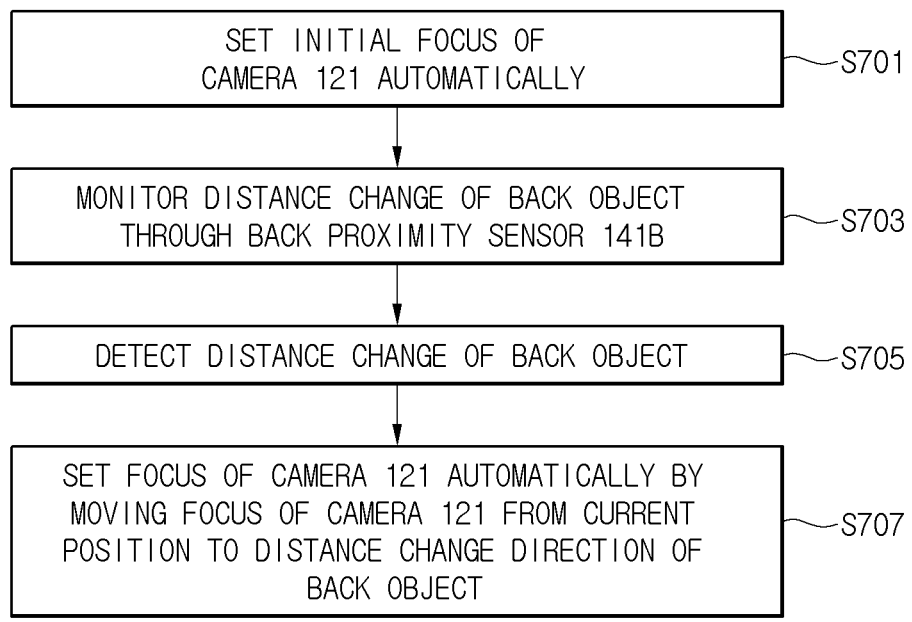
FIG. 28 is a flowchart illustrating an automatic focus adjustment scenario a mobile terminal according to an embodiment of the present invention.

FIG. 28 is a flowchart illustrating an automatic focus adjustment scenario of a mobile terminal according to an embodiment of the present invention.

The control unit 180 adjusts the initial focus of the camera 121 automatically in operation S701.

According to an embodiment of the present invention, after the control unit 180 sets a focus to infinity and moves it to the minimum point to determine a point that contrast is the maximum, it may set the point that contrast is the maximum as a focus.

According to an embodiment of the present invention, after the control unit 180 set a focus to infinity and moves it to the minimum point to determine a point that contrast is the maximum, it may set the point that contrast is the maximum as a focus. In this case, a time of automatic focus adjustment may be reduced. Also, it is possible to perform a relatively accurate automatic focus adjustment in a dark environment.

While the initial focus of the camera 121 is set, the control unit 180 may monitor a distance change of a back object through the back proximity sensor 141b in operation S703.

When the distance change of the back object occurs in operation S705, the control unit 180 automatically sets the focus of the camera 121 while moving the focus of the camera 121 in a direction of the distance change of the back object from a current point. For example, when the back object becomes away from the camera 121, the control unit 180 may set the focus of the camera 121 automatically while moving the focus of the camera 121 in a direction away from the current point. Through this, since the control unit 80 automatically sets the focus of the camera 121 while moving the focus in one direction, a fast automatic focus adjustment is possible.

According to the present invention, it is very important to accurately know whether an object, that is, a capturing target, becomes away from or close to the camera 121 by using the back proximity sensor during a camera focus process. In the case of a camera, a reciprocating movement of a camera actuator, for example, setting a focus in a direction from far to close or on the contrary, in a direction from close to far, in order to set the focus is general.

Additionally, in the description for FIG. 28, a distance to an object measured by a back proximity sensor is used during camera capturing but a front proximity sensor may be used for distance measurement. That is, when image capturing is performed by a front camera of a terminal, a front proximity sensor operates and monitors a distance to an object, so that a direction for setting the focus (for example, the object moves away from or close to the front camera) may be determined.

Figure 29A:
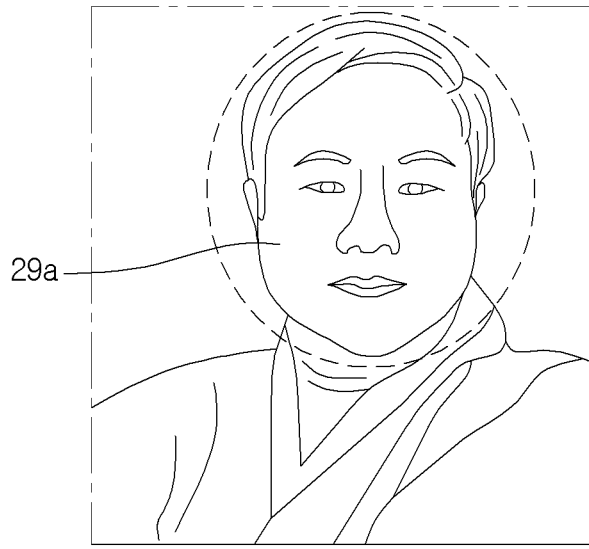
FIGS. 29A and 29B are views when a focus is adjusted during camera capturing by using a mobile terminal according to an embodiment of the present invention.
Figure 29B:
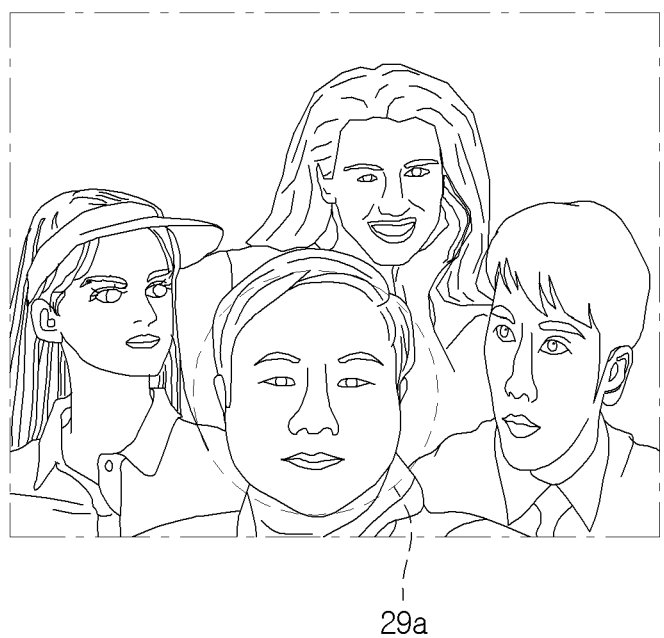

FIGS. 29A and 29B are views when a focus is adjusted during camera capturing by using a mobile terminal according to an embodiment of the present invention.

A user may set the focus on a specific object by using a front proximity sensor or a back proximity sensor during camera capturing. For example, when a user takes a picture with several people, the focus is set on the user's face.

First, the user allows only the user's face to be focused by a front camera or a back camera. This is for setting an object to be traced, that is, an object to be focused.

At this point, the control unit 180 of a terminal detects a distance to an object (for example, a face) measured by the front or back proximity sensor and when a corresponding object (for example, a face) moves or another object (for example, another person's face) is focused by a camera, a predetermined object (for example, a face) is distinguished from another object (for example, another person's face) and a focus is set on the predetermined object (for example, a face).

For example, as shown in FIG. 29A, when only one person's face is focused by a camera, the control unit detects a distance with the corresponding object (for example, a user's face) 29*a* by using the front proximity sensor or the back proximity sensor. Then, as shown in FIG. 29B, when another person's face other than the corresponding user face is focused, the control unit 180 traces a movement of the predetermined object (for example, the user's face) and set the focus of the camera according to the movement of the corresponding user face.

As a result, even when a plurality of users are focused by the camera, the trace of a specific user (that is, a predetermined object) is focused very fast.

Then, a self camera control scenario of the mobile terminal 100 according to an embodiment of the present invention is described with reference to FIGS. 30 and 31.

Figure 30:
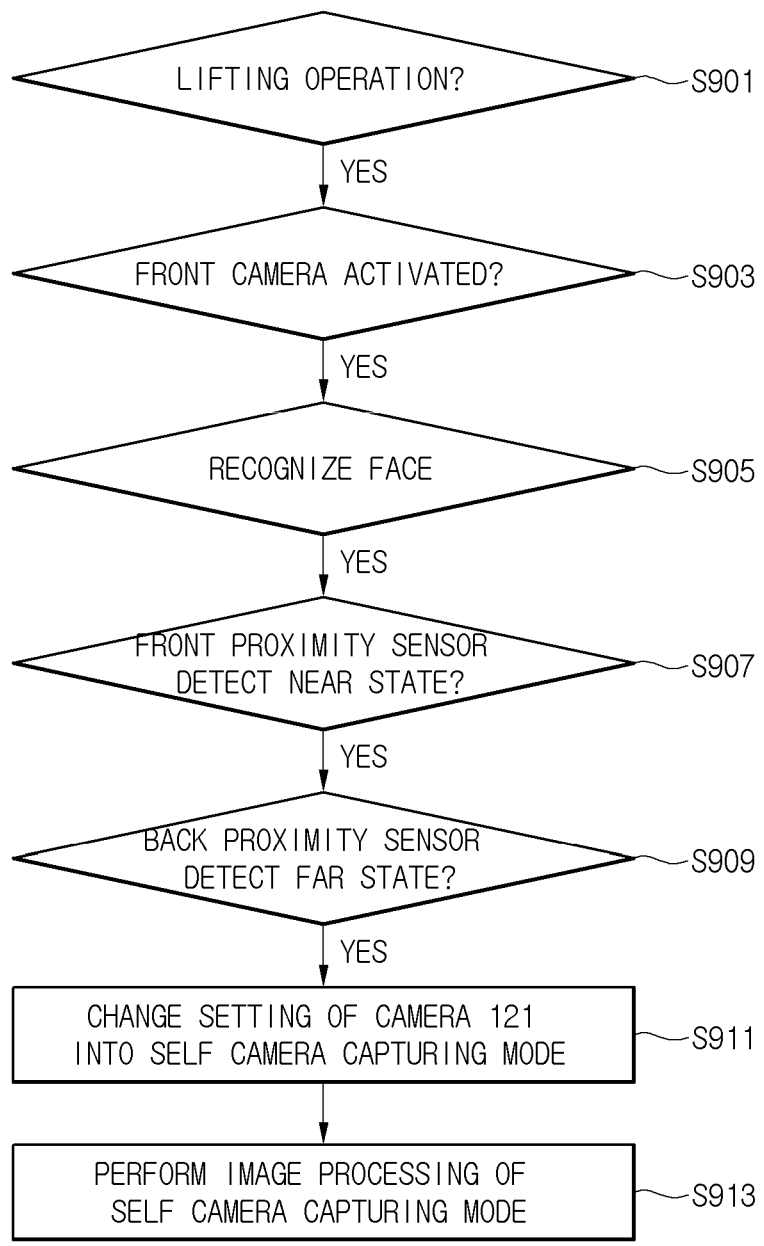
FIG. 30 is a flowchart illustrating a self camera control scenario of a mobile terminal according to an embodiment of the present invention.
Figure 31:
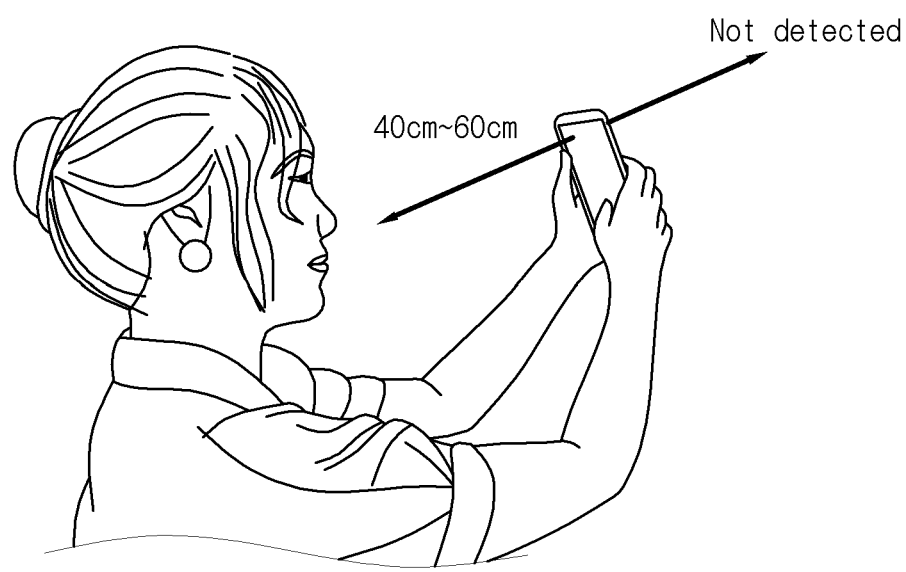
FIG. 31 is a view when a user performs image capturing in a self camera mode according to an embodiment of the present invention.

FIG. 30 is a flowchart illustrating a self camera control scenario of a mobile terminal according to an embodiment of the present invention. FIG. 31 is a view when a user performs image capturing in a self camera mode according to an embodiment of the present invention.

The control unit 180 checks whether an operation for lifting the mobile terminal 100 is detected in operation S901. For example, when a state that the tremor of the control unit 180 is not detected changes into a state that the tremor of the control unit 180 is detected, by the acceleration sensor 142, or the proximity of an object changes from NEAR to FAR detected by the back proximity sensor 141*b*, the control unit 180 may determine this case as a gesture for lifting a terminal by a user.

Then, the control unit 180 checks whether a currently activated camera is a front camera in operation S903.

The control unit 180 checks whether a face is recognized from an image obtained through the camera 121 in operation S905.

The control unit 180 checks whether the front proximity sensor 141*a* detects a NEAR state in operation S907.

The control unit 180 checks whether the back proximity sensor 141*b* detects a FAR state in operation S909.

When an operation for lifting the mobile terminal 100 is detected, a currently activated camera is a front camera, a face is recognized from an image obtained through the camera 121, the front proximity sensor 141*a* detects a NEAR state, and the back proximity sensor 141*b* detects a FAR state, the control unit 180 changes a setting of the camera 121 into a self camera capture mode in operation S911 and performs image processing of a self camera capture mode on an image obtained through the camera 121 in operation S913. According to embodiments of the present invention, a back proximity sensor and a front proximity sensor are configured to determine an object placed within a range of about 40 cm to about 60 cm as NEAR and also a distance determined as NEAR may be adjusted according to other embodiments.

Figure 32:
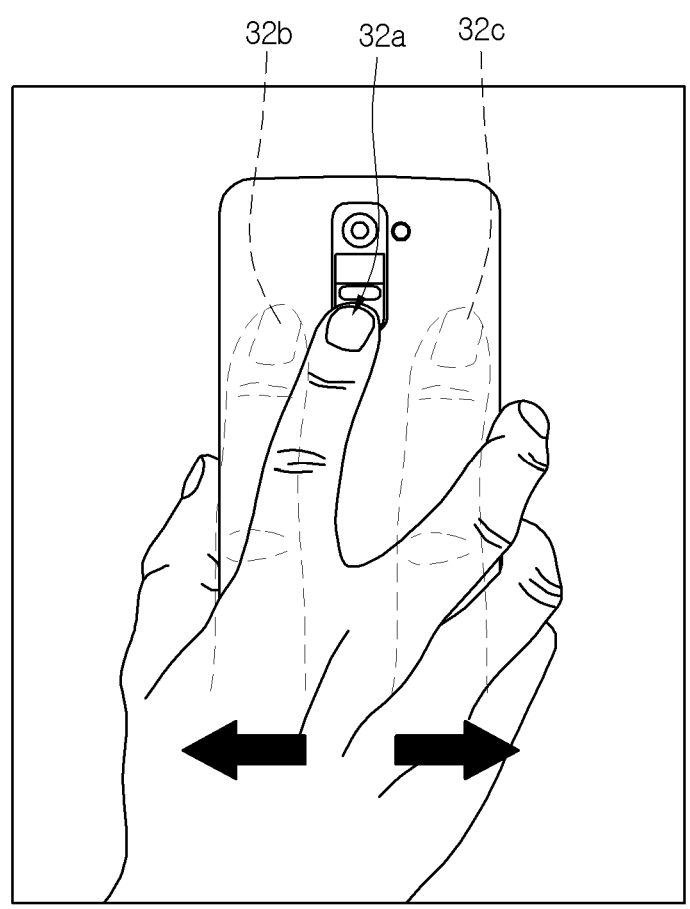
FIG. 32 is a view when a movement of a user's finger is captured on a back proximity sensor and accordingly, an operation of a terminal is controlled according to an embodiment of the present invention.

FIG. 32 is a view when a movement of a user's finger is captured on a back proximity sensor and accordingly, an operation of a terminal is controlled according to an embodiment of the present invention.

The back proximity sensor 141*b* in this embodiment, as described above, may be configured with a light receiving unit including a plurality of photo diodes and may capture the position of an object and a movement of an object. In this case, the control unit 180 of a terminal may control an operation of the terminal in various ways on the basis of that the user's finger moves from a predetermined position 32*a* to a first direction 32*b* or a second direction 32*c*. For example, the control unit 180 may perform a function, for example, adjusting the volume of music or video or back and forward of an internet application.

Figure 33A:
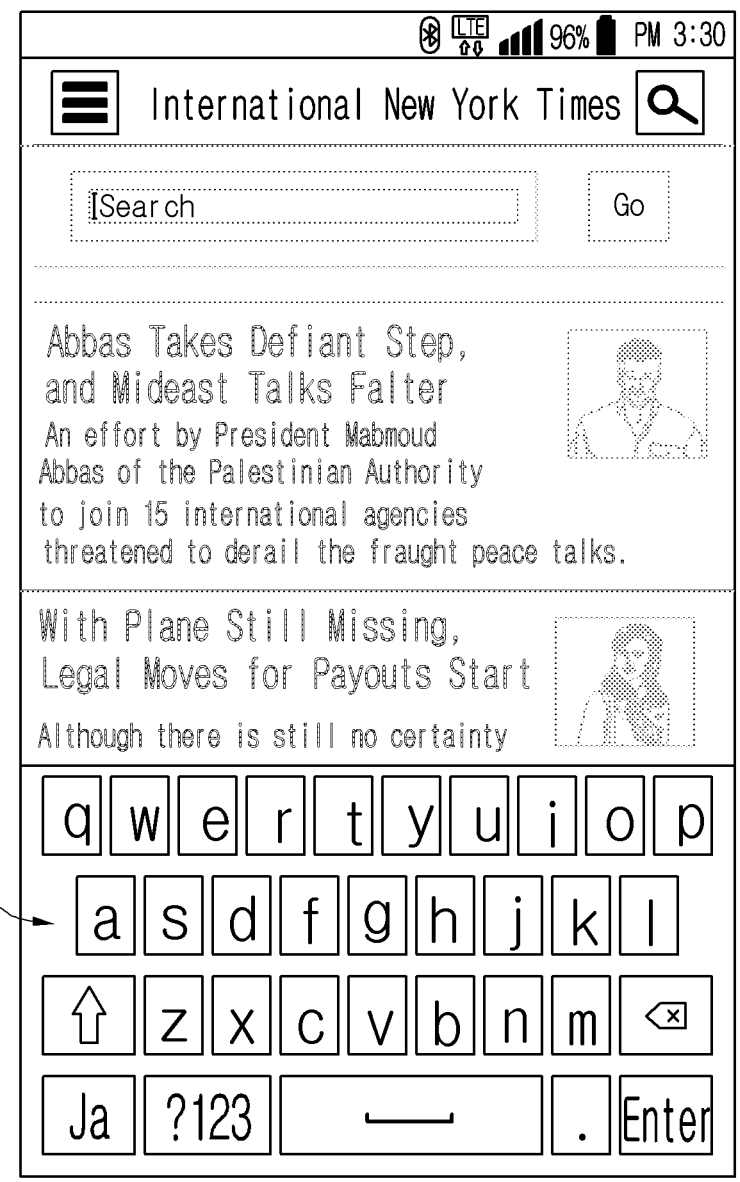
FIGS. 33A and 33B are views when a screen UI changes according to user's heat rate information in a mobile terminal according to an embodiment of the present invention.
Figure 33B:

FIGS. 33A and 33B are views when a screen UI changes according to user's heat rate information in a mobile terminal according to an embodiment of the present invention.

While a terminal checks user's heart rate information, it is possible to change at least part of UIs displayed on a screen. For example, as shown in FIG. 33A, when a user inputs a text by using the virtual keyboard 33*a*, if a difference occurs between the user's heart rate measured by the control unit 180 and a predetermined value, according to the difference, it is possible to change the size of the virtual keyboard 33*a*. If the user's heart rate measured by the control unit 180 is greater than the predetermined value and it is determined that the user is in an exited state, the control unit 180 may display a larger size of the virtual keyboard 33*b* on a screen. When a user inputs a text by manipulating a virtual keyboard after a vigorous workout or in an actual exited state, a typo is more likely to occur, so that it is desirable to change the size of the virtual keyboard.

Then, according to a user's heart rate state, the control unit 180 may also change the position of the virtual keyboard.

Then, on the basis of the measured heart rate information, a scenario for managing an application is described. A mobile terminal according to an embodiment of the present invention may store or manage the user's measured heart rate information and for this, the control unit 180 of the terminal may store information on an application in execution on the basis of the measured heart rate information.

FIG. 34 is a view illustrating statistics of heart rate information measured by a mobile terminal according to an embodiment of the present invention. FIGS. 35A to 36B are views illustrating various UIs for controlling an application on the basis of heart rate information according to an embodiment of the present invention.

A user may measure a heart rate while making a phone call or listening to music. For example; when a sensor for measuring a heart rate is disposed at the terminal back, a user may measure a heart rate naturally while manipulating the terminal.

When the user wants to check the stored heart rate information, the control unit 180 may display related application information in addition to the stored heart rate information. For example, as shown in FIG. 34, an emotion state menu 34*a* representing a classification for the measured heart rate information and an application information menu 34*b* representing information on an application executed in each emotion state UI may be displayed.

Especially, the control unit 180 of the terminal according to an embodiment of the present invention may control a corresponding application as a background on the basis of heart rate information measured during the executions of various applications. For example, when a phone application is executed and a user makes a phone call, in the case that the measured heart rate is greater than a predetermined value, the control unit 180 may classify it as 'stress' and may record a phone call automatically. Then, when a music application is executed and a user listens to music, in the case that the measured heart rate is less than a predetermined value, the control unit 180 may classify it as 'peaceful' and may record information on music played in a music application and information on an interval of corresponding music.

If a user wants to check details on a call application classified as 'stress' through the emotion state menu 34*a*, the control unit 180 may display content on that a high heart rate is measured during the execution of a corresponding phone application. As shown in FIG. 35A, the control unit 180 may display information on a date on which a high heart rate is measured and the degree of stress in a corresponding phone application. Then, when a high heart rate is measured during a call, the control unit 180 may store call content automatically and a user may check the stored call content later.

When a user wants to check call content in which a high heart rate is measured, the control unit 180, as shown in FIG. 35B, may display a heart rate change graph 35*a* displaying changes in heart rate while a call application is executed.

Then, the control unit 180 may display a position classified as 'stress' when a heart rate is greater than a predetermined value, in addition to information on words relating to a corresponding interval. For example, words 35*b* and 35*c* classified based on heart rate information may be displayed.

Figures 35C, 36A:
FIGS. 35A to 36B are views illustrating various UIs for controlling an application on the basis of heart rate information according to an embodiment of the present invention.

Additionally, when a user's heart rate changes more than a predetermined range during application execution, the control unit 180 may control a corresponding application automatically and for example, as shown in FIG. 35C, may perform call recording automatically when a change of a heart rate is great during a phone call.

As another embodiment, the case in which a user checks details on a music application among applications that the user classifies as 'peaceful' in the heart rate statistics information shown in FIG. 34 will be described.

When a music application is executed and a user listens to music, in the case that a measured heart rate is less than a heart rate set as a peaceful state, the control unit 180 may classify it as 'peaceful' and also may store information on music of the music application executed at that moment. Then, the control unit 180 may display information on stored music and information stored weather through a UI shown in FIG. 36A.

Figure 36B:
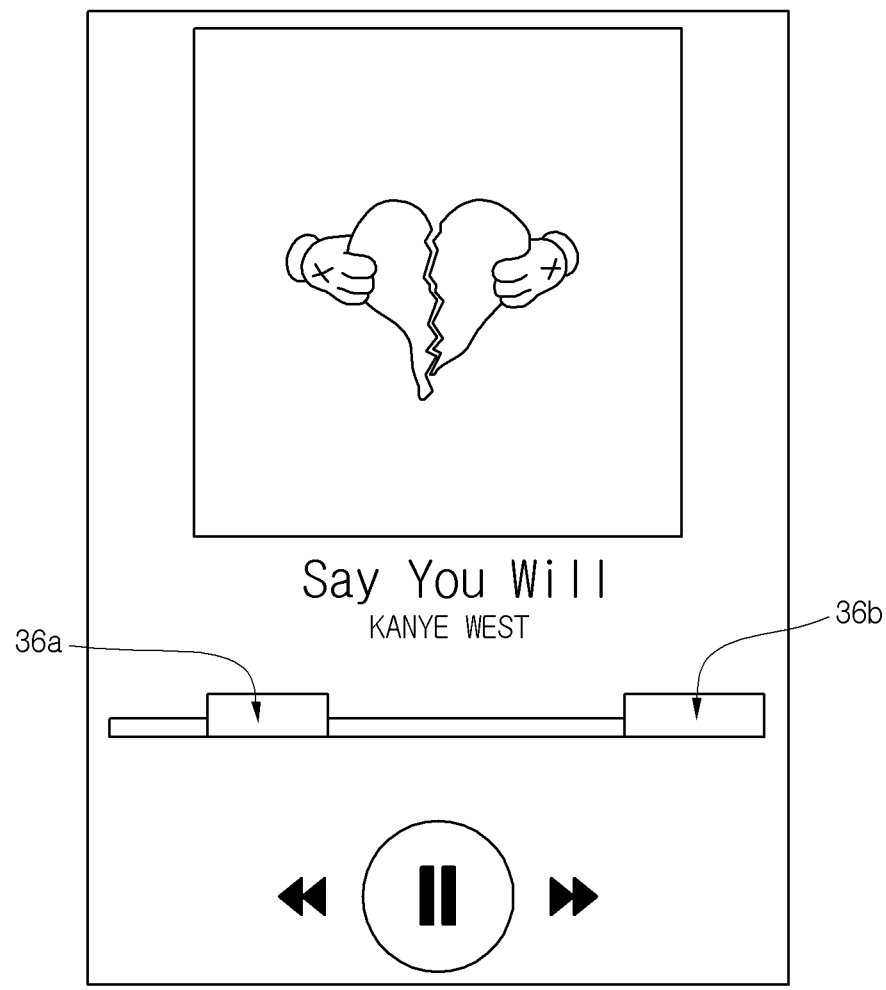

Then, when a user selects a specific item from hourly information on a displayed music application, the control unit 180 may display a stored music interval in the music application. For example, as shown in FIG. 36B, additional tags 36*a* and 36*b* may be displayed in a music UI, with respect to an interval at which a user feels a peaceful emotion.

Additionally, the control unit 180 may record emotion information (for example, stress or peaceful) based on a user's heart rate and also may share such recorded information between users, with respect to the music stored in a music application or connectable.

Then, a video playback scenario of the mobile terminal 100 according to an embodiment of the present invention will be described with reference to FIG. 37.

Figure 37:
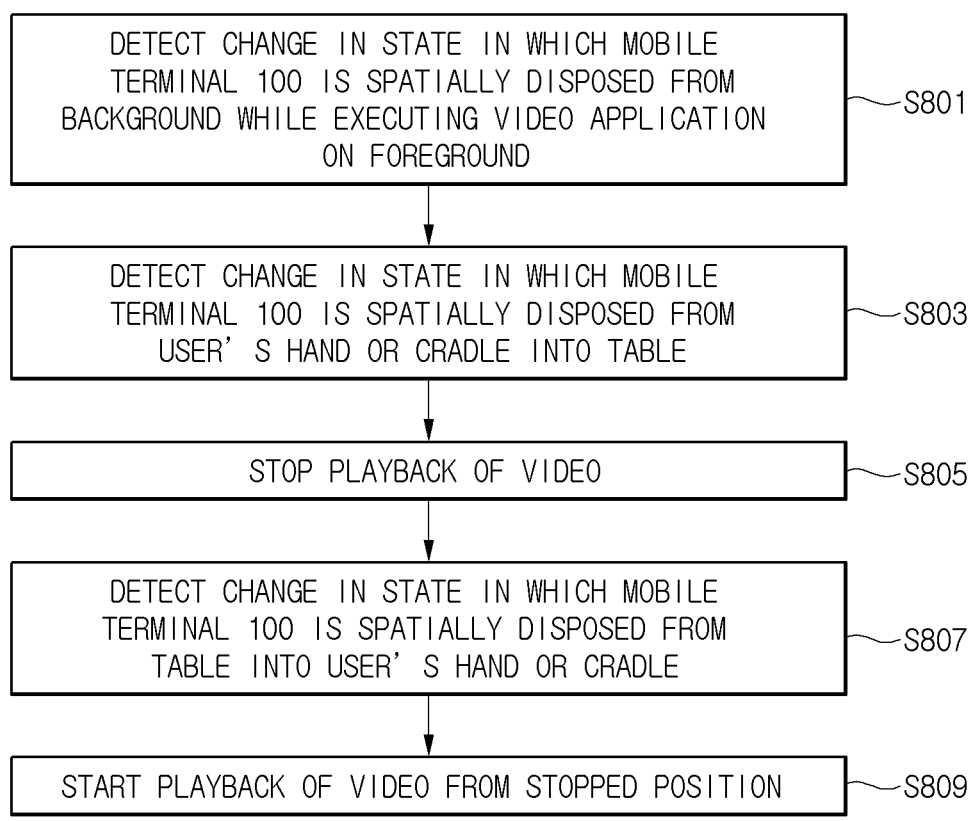
FIG. 37 is a flowchart illustrating a video playback scenario of a mobile terminal according to an embodiment of the present invention.

FIG. 37 is a flowchart illustrating a video playback scenario of a mobile terminal according to an embodiment of the present invention.

The control unit 180 detects a change in state in which the mobile terminal 100 is spatially placed while executing a video application in a foreground in operation S801.

If the state in which the mobile terminal 100 is spatially placed changes from the user's hand or a cradle into a table in operation S803, the control unit 180 stops the playback of the video in operation S805.

If the state in which the mobile terminal 100 is spatially placed changes from a table into the user's hand or a cradle in operation S807, the control unit 180 starts to play a video from the stopped position in operation S809.

As described above, whether the state in which the mobile terminal 100 is spatially placed corresponds to the user's hand may be determined on the basis of a trembling pattern.

If the trembling pattern is not detected, whether the state in which the mobile terminal 100 is spatially placed corresponds to a cradle or a table may be determined on the basis of whether the mobile terminal is parallel to the ground.

When the trembling pattern is detected while the playback of a video stops, it is regarded that a user intends to watch the video and thus, the control unit 180 starts the playback of the video.

While the playback of the video stop, if the mobile terminal 100 is not parallel to the ground and an angle between the mobile terminal 100 and the ground is more than a reference angle, it is regarded that a user intends to watch the video and thus, the control unit 180 starts the playback of the video.

While the video is played, if a table state is detected, it is regarded that a user does not intend to watch the video and thus, the control unit 180 stops the playback of the video.

According to the mobile terminal suggested above, more convenient functions may be provided depending on a state or spatial position of the mobile terminal.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A mobile terminal comprising:
   a display unit disposed at a front of the mobile terminal;
   a front proximity sensor disposed at the front of the mobile terminal;
   a back proximity sensor disposed at a back of the mobile terminal; and
   a control unit performing an operation by using a detection result of the back proximity sensor,
   wherein the back proximity sensor performs a role of a heart rate sensor, and
   wherein the control unit stores information on a user's heart rate measured by the back proximity sensor and controls an operation of a currently running application according to the user's heart rate.

2. The mobile terminal according to claim 1, wherein the control unit controls an operation of the mobile terminal by using a detection result of both the front proximity sensor and the back proximity sensor.

3. The mobile terminal according to claim 2, wherein the control unit determines a state in which the mobile terminal is disposed spatially according to whether there is an object through the front proximity sensor and the back proximity sensor and controls an operating state of the mobile terminal according to the determination result.

4. The mobile terminal according to claim 3, wherein when a running application is a phone application, if a spatial state of the mobile terminal determined through the front proximity sensor and the back proximity sensor is changed, the control unit changes a phone call mode automatically between a headset mode and a speaker phone mode.

5. The mobile terminal according to claim 3, wherein when a spatial state of the mobile terminal determined through the front proximity sensor and the back proximity sensor is changed, the control unit may automatically hide a soft key corresponding to a user input key displayed in a screen or displays the soft key in the screen.

6. The mobile terminal according to claim 3, wherein when a spatial state of the mobile terminal determined through the front proximity sensor and the back proximity sensor is changed, the control unit displays a virtual keyboard for allowing a user to input a text in a screen or hides the virtual keyboard.

7. The mobile terminal according to claim 3, wherein the control unit continuously or periodically checks whether there is a proximity of an object through the back proximity sensor and when a predetermined application is running, if the proximity of the object is checked by the back proximity sensor, displays warning information through the display unit.

8. The mobile terminal according to claim 3, wherein the control unit continuously or periodically checks whether there is a proximity of an object through the back proximity sensor and when a predetermined application is running, if the proximity of the object is checked by the back proximity sensor, stops an operation of the running application.

9. The mobile terminal according to claim 1, wherein the back proximity sensor obtains a photoplethysmographic (PPG) signal of a user by emitting light to a portion of a human body.

10. The mobile terminal according to claim 9, further comprising at least one back key disposed at the back of the mobile terminal and manipulated by a user.

11. The mobile terminal according to claim 10, wherein the back proximity sensor comprises a light emitting device emitting light, a light receiving device receiving light emitted from the light emitting device, and a partition wall disposed between the light emitting device and the light receiving device, and
wherein light generated from the light emitting device is emitted to an object through the back key.

12. The mobile terminal according to claim 11, wherein the back proximity sensor further comprises a front glass forming a portion of the back key, and
wherein the light receiving device comprises a plurality of photo diodes.

13. The mobile terminal according to claim 1, wherein when the currently running application is a phone application, the control unit performs call recording automatically according to the user's heart rate.

14. The mobile terminal according to claim 1, wherein when the currently running application is a music application, the control unit stores information on music played through the music application according to the user's heart rate.

15. A mobile terminal comprising:
a display unit disposed at a front of the mobile terminal;
a proximity sensor disposed at the front of the mobile terminal;
a heart rate sensor disposed at a back of the mobile terminal and measuring a PPG signal by emitting light to a body portion of a user; and
a control unit checking a user's heart rate from the PPG signal measured by the heart rate sensor and according thereto, controlling an operation of the mobile terminal.

16. The mobile terminal according to claim 15, wherein when a phone application is running and a phone connection is established with a second mobile terminal, the control unit transmits information on the user's heart rate measured through the heart rate sensor to the second mobile terminal.

17. The mobile terminal according to claim 15, wherein when a call signal for requesting a phone connection from the second mobile terminal is received, the control unit displays information on a user's heart rate of the second mobile terminal as an image or a text on a screen of the display unit.

18. The mobile terminal according to claim 15, wherein the control unit classifies a user's emotion state from the measured PPG signal and stores information on an application running according to each classified emotion state.

* * * * *